US011524985B2

(12) United States Patent
Kalabokis et al.

(10) Patent No.: US 11,524,985 B2
(45) Date of Patent: Dec. 13, 2022

(54) IL-37 FUSION PROTEIN AND METHODS OF MAKING AND USING SAME

(71) Applicants: BIO-TECHNE CORPORATION, Minneapolis, MN (US); THE REGENTS OF THE UNIVERSITY OF COLORADO, Denver, CO (US)

(72) Inventors: Vassilios Kalabokis, Fridley, MN (US); Charles A. Dinarello, Denver, CO (US)

(73) Assignees: Bio-Techne Corporation, Minneapolis, MN (US); The Regents of the University of Colorado, Denver, CO (US)

( * ) Notice: Subject to any disclaimer, the term of this patent is extended or adjusted under 35 U.S.C. 154(b) by 97 days.

(21) Appl. No.: 16/492,666

(22) PCT Filed: Mar. 20, 2018

(86) PCT No.: PCT/US2018/023311
§ 371 (c)(1),
(2) Date: Sep. 10, 2019

(87) PCT Pub. No.: WO2018/175403
PCT Pub. Date: Sep. 27, 2018

(65) Prior Publication Data
US 2020/0055911 A1 Feb. 20, 2020

Related U.S. Application Data

(60) Provisional application No. 62/589,760, filed on Nov. 22, 2017, provisional application No. 62/473,878, filed on Mar. 20, 2017.

(51) Int. Cl.
C07K 14/54 (2006.01)
A61K 38/00 (2006.01)
A61P 11/06 (2006.01)

(52) U.S. Cl.
CPC .............. C07K 14/54 (2013.01); A61P 11/06 (2018.01); A61K 38/00 (2013.01); C07K 2319/30 (2013.01)

(58) Field of Classification Search
None
See application file for complete search history.

(56) References Cited

U.S. PATENT DOCUMENTS

2009/0074710 A1\* 3/2009 Dinarello .................. A61P 1/04
424/85.2
2009/0264627 A1\* 10/2009 Gillies ............... A61K 47/6851
530/387.3

FOREIGN PATENT DOCUMENTS

CN 106581643 A 4/2017
WO WO 2013/184942 A1 12/2013
WO WO 2016/201503 A1 12/2016

OTHER PUBLICATIONS

Boraschi et al., IL-37: a new anti-inflammatory cytokine of the IL-1 family. Eur Cytokine Netw. 2011, vol. 2(3), p. 127-47 (Year: 2011).\*
Schlothauer (Protein Eng Des Sel. Oct. 2016;29(10):457-466. Epub Aug. 29, 2016) (Year: 2016).\*
Chen et al (Adv Drug Deliv Rev. Oct. 15, 2013; 65(10): 1357-1369) (Year: 2013).\*
Onu et al (J Immunol Jan. 1, 1997, 158 (1) 255-262) (Year: 1997).\*
ACRO Biosystems, IL-37, His Tag (ILB-H5141), available online at https://www.acrobiosystems.com/P1660-Human-IL-37--IL-1F7b-Protein-His-Tag.html (Retrieved on Mar. 14, 2021).
AdipoGen Life Sciences, IL-37 (aa 46-218) (human) (rec.) (His), Product Data Sheet, available online at https://adipogen.com/chi-ag-40a-0174-il-37-aa-46-218-human-rec-his.html (Retrieved on Mar. 14, 2021).
Alagbe et al., Interleukin-27 and interleukin-37 are elevated in sickle cell anemia patients and inhibit in vitro secretion of interleukin-8 in neutrophils and monocytes. *Cytokine* 107, 85-92 (2018).
Allam et al., Association of IL-37 gene polymorphisms with susceptibility to tuberculosis in Saudi subjects. *Microbiol Immunol* 60, 778-786 (2016).
Anuradha et al., Modulation of CD4(+) and CD8(+) T Cell Function and Cytokine Responses in Strongyloides stercoralis Infection by Interleukin-27 (IL-27) and IL-37. *Infect Immun* 85, e00500-17 (2017).
Ballak et al., IL-37 protects against obesity-induced inflammation and insulin resistance. *Nat Commun* 5, 4711 (2014).
Bao et al., Variations of chromosome 2 gene expressions among patients with lung cancer or non-cancer. *Cell Biol Toxicol* 32, 419-435 (2016).
Bello et al., The Role, Involvement and Function(s) of Interleukin-35 and Interleukin-37 in Disease Pathogenesis. *Int J Mol Sci* 19, 1149 (2018).
Berraies et al., Increased expression of thymic stromal lymphopoietin in induced sputum from asthmatic children, *Immunol Lett* 178, 85-91 (2016).
Boraschi et al., IL-37: a new anti-inflammatory cytokine of the IL-1 family. *Eur Cytokine Netw* 22, 127-147 (2011).
Bufler et al., A complex of the IL-1 homologue IL-1F7b and IL-18-binding protein reduces IL-18 activity. *Proc Natl Acad Sci U S A* 99, 13723-13728 (2002).
Caraffa et al., New concepts in neuroinflammation: mast cells pro-inflammatory and anti-inflammatory cytokine mediators. *J Biol Regul Homeost Agents* 32, 449-454 (2018).

(Continued)

*Primary Examiner* — Brian Gangle
*Assistant Examiner* — Andrea K McCollum
(74) *Attorney, Agent, or Firm* — Mueting Raasch Group

(57) ABSTRACT

The disclosure provides interleukin 37 (IL-37) fusion proteins, methods of making IL-37 fusion proteins including constructs used to express IL-37 fusion proteins, and methods of using IL-37 fusion proteins. In some embodiments, the IL-37 fusion protein includes amino acids 46-206 of isoform B of IL-37 and a heavy chain portion of an antibody.

13 Claims, 27 Drawing Sheets

Specification includes a Sequence Listing.

(56) References Cited

OTHER PUBLICATIONS

Carinci et al., Mast cell and cancer with special emphasis on il-37 an anti-inflammatory and inhibitor of innate immunity: new frontiers. *J Biol Regul Homeost Agents* 30, 945-950 (2016).
Cavalli et al., Suppression of inflammation and acquired immunity by IL-37. *Immunol Rev* 281, 179-190 (2018).
Cavalli et al., Interleukin 37 reverses the metabolic cost of inflammation, increases oxidative respiration, and improves exercise tolerance. *Proc Natl Acad Sci U S A* 114, 2313-2318 (2017) + Supplemental Information (2 pages).
Cavalli et al., Treating experimental arthritis with the innate immune inhibitor interleukin-37 reduces joint and systemic inflammation. *Rheumatology (Oxford)* 55, 2220-2229 (2016).
Chen et al., Effects of exogenous IL-37 on the biological characteristics of human lung adenocarcinoma A549 cells and the chemotaxis of regulatory T cells. *Cancer Biomark* 21, 661-673 (2018).
Chen et al., CCL22 and IL-37 inhibit the proliferation and epithelial-mesenchymal transition process of NSCLC A549 cells. *Oncol Rep* 36, 2017-2024 (2016).
Coll-Miro et al., Beneficial effects of IL-37 after spinal cord injury in mice. *Proc Natl Acad Sci U S A* 113, 1411-1416 (2016).
Conti et al., Impact of mast cells in mucosal immunity of intestinal inflammation: Inhibitory effect of IL-37, *Eur J Pharmacol* 818, 294-299 (2018).
Conti et al., Potential therapeutic use of IL-37: a key suppressor of innate immunity and allergic immune responses mediated by mast cells. *Immunol Res* 65, 982-986 (2017).
Conti et al., Mast cells emerge as mediators of atherosclerosis: Special emphasis on IL-37 inhibition. *Tissue Cell* 49, 393-400 (2017).
Conti et al., IL-37 a New IL-1 Family Member Emerges as a Key Suppressor of Asthma Mediated by Mast Cells. *Immunol Invest* 46, 239-250 (2017).
De Lorenzi et al., Evidence that the Human Innate Immune Peptide LL-37 may be a Binding Partner of Amyloid-beta and Inhibitor of Fibril Assembly. *J Alzheimers Dis* 59, 1213-1226 (2017).
Dinarello et al., Suppression of innate inflammation and immunity by interleukin-37. *Eur J Immunol* 46, 1067-1081 (2016).
Ding et al., IL-37 is associated with osteoarthritis disease activity and suppresses proinflammatory cytokines production in synovial cells. *Sci Rep* 7, 11601 (2017).
Ding et al., Outcomes of Interferon/Ribavirin Therapy in Patients with HCV Defined by Expression of Plasma Soluble Human Leukocyte Antigen-G but Not IL-37. *Med Sci Monit* 22, 1398-1402 (2016).
Ding et al., The novel role of IL-37 in prostate cancer: evidence as a promising radiosensitizer. *Med Oncol* 35, 6 (2017).
Ding et al., The role of IL-37 in cancer, *Med Oncol* 33, 68 (2016).
Elenius et al., The relationship of serum vitamins A, D, E and LL-37 levels with allergic status, tonsillar virus detection and immune response. *PLoS One* 12, e0172350 (2017).
Ellisdon et al., Homodimerization attenuates the anti-inflammatory activity of interleukin-37, *Sci Immunol* 2, eaaj 1548 (2017).
Fawzy et al., Serum Level of Interleukin-37 and Expression of Its mRNA in Ankylosing Spondylitis Patients: Possible Role in Osteoporosis. *Egypt J Immunol* 23, 19-29 (2016).
Gao et al., Development and characterization of monoclonal antibody against human IL-37b. *Cytotechnology* 69, 217-227 (2017).
Ge et al., Interleukin-37 suppresses tumor growth through inhibition of angiogenesis in non-small cell lung cancer, *J Exp Clin Cancer Res* 35, 13 (2016).
Godsell et al., Clinical associations of IL-10 and IL-37 in systemic lupus erythematosus. *Sci Rep* 6, 34604 (2016).
Grabherr et al., Ethanol-mediated suppression of TL-37 licenses alcoholic liver disease. *Liver Int* 38, 1095-1101 (2018).
Gunaltay et al., Reduced IL-37 Production Increases Spontaneous Chemokine Expressions in Colon Epithelial Cells. *Dig Dis Sci* 62, 1204-1215 (2017).
Hahn et al., The novel interleukin-1 cytokine family members in inflammatory diseases. *Curr Opin Rheumatol* 29, 208-213 (2017).

Hoeke et al., The Effects of Selective Hematopoietic Expression of Human IL-37 on Systemic Inflammation and Atherosclerosis in LDLr-Deficient Mice. *Int J Mol Sci* 18, 1672 (2017).
Hu, Role of Anti-inflammatory Cytokines IL-35 and IL-37 in Asthma. *Inflammation* 40, 697-707 (2017).
Hu et al., Protective effect of TM6 on LPS-induced acute lung injury in mice, *Scientific Reports* 7, 572 (2017).
Huang et al., Protective effect of the polarity of macrophages regulated by IL-37 on atherosclerosis. *Genet Mol Res* 15, gmr7616 (2016).
Huang et al., Interleukin-37 alleviates airway inflammation and remodeling in asthma via inhibiting the activation of NF-kappaB and STAT3 signalings. *Int Immunopharmacol* 55, 198-204 (2018).
Huang et al., HIV-1 TAT peptide-human IL-37-IGG1 Fc region fusion protein, SEQ ID 4., XP2800779A, CN106581643-A, Apr. 26, 2017, 1 page.
Huo et al., Elevated serum interleukin-37 level is a predictive biomarker of poor prognosis in epithelial ovarian cancer patients. *Arch Gynecol Obstet* 295, 459-465 (2017).
Jia et al., Reviews of Interleukin-37: Functions, Receptors, and Roles in Diseases. *Biomed Res Int* 2018, 3058640 (2018).
Jiang et al., Decreased expression of interleukin-37 in the ectopic and eutopic endometria of patients with adenomyosis. *Gynecol Endocrinol* 34, 83-86 (2018).
Joosten et al., Alpha-1-anti-trypsin-Fc fusion protein ameliorates gouty arthritis by reducing release and extracellular processing of IL-1beta and by the induction of endogenous IL-1Ra. *Ann Rheum Dis* 75, 1219-1227 (2016).
Kaabachi et al., Interleukin-26 is overexpressed in Behcet's disease and enhances Th17 related-cytokines. *Immunol Lett* 190, 177-184 (2017).
Kaabachi et al., Interleukin-37 in endometriosis. *Immunol Lett* 185, 52-55 (2017).
Kaplanski, Interleukin-18: Biological properties and role in disease pathogenesis. *Immunol Rev* 281, 138-153 (2018).
Kim et al., Interleukin-37 Relieves Allergic Inflammation in a House Dust Mite Allergic Rhinitis Murine Model. *Iran J Allergy Asthma Immunol* 16, 404-417 (2017).
Kumar et al., Interleukin-1F7B (IL-1H4/IL-1F7) is processed by caspase-1 and mature IL-1F7B binds to the IL-18 receptor but does not induce IFN-gamma production. *Cytokine* 18, 61-71 (2002).
Li et al., Interleukin-37 suppresses the inflammatory response to protect cardiac function in old endotoxemic mice. *Cytokine* 95, 55-63 (2017).
Li et al., Extracellular forms of IL-37 inhibit innate inflammation in vitro and in vivo but require the IL-1 family decoy receptor IL-1R8. *Proc Natl Acad Sci U S A* 112, 2497-2502 (2015).
Li et al., [Interleukin-37 induces apoptosis and autophagy of SMMC-7721 cells by inhibiting phosphorylation of mTOR], *Xi Bao Yu Fen Zi Mian Yi Xue Za Zhi* 33, 440-445 (2017), Abstract Only.
Li et al., IL-37 induces autophagy in hepatocellular carcinoma cells by inhibiting the PI3K/AKT/mTOR pathway. *Mol Immunol* 87, 132-140 (2017).
Li et al., The Low Expression of IL-37 Involved in Multiple Myeloma—Associated Angiogenesis. *Med Sci Monit* 22, 4164-4168 (2016).
Lin et al., Interleukin-37 expression and its potential role in oral leukoplakia and oral squamous cell carcinoma. *Sci Rep* 6, 26757 (2016).
Lin et al., Association between interleukin 37 (rs3811047) polymorphism and multiple autoimmune diseases in a Chinese population: A PRISMA-compliant meta-analysis. *Medicine (Baltimore)* 97, e0386 (2018).
Liu et al., Interleukin-37: a new molecular target for host-directed therapy of tuberculosis. *Future Microbiol* 12, 465-468 (2017).
Liu et al., IL-37 Confers Protection against Mycobacterial Infection Involving Suppressing Inflammation and Modulating T Cell Activation. *PLoS One* 12, e0169922 (2017).
Liu et al., Transgenic Overexpression of IL-37 Protects Against Atherosclerosis and Strengthens Plaque Stability. *Cell Physiol Biochem* 45, 1034-1050 (2018).

(56) References Cited

OTHER PUBLICATIONS

Liu et al., IL-37 increased in patients with acute coronary syndrome and associated with a worse clinical outcome after ST-segment elevation acute myocardial infarction, *Clin Chim Acta* 468, 140-144 (2017).
Liu et al., Interleukin 37 limits monosodium urate crystal-induced innate immune responses in human and murine models of gout. *Arthritis Res Ther* 18, 268 (2016).
Liu et al., IL-37 suppresses hepatocellular carcinoma growth by converting pSmad3 signaling from JNK/pSmad3L/c-Myc oncogenic signaling to pSmad3C/P21 tumor-suppressive signaling, *Oncotarget* 7, 85079-85096 (2016).
Liuqing et al., Elevated IL-37, IL-18 and IL-18BP serum concentrations in patients with primary Sjogren's syndrome. *J Investig Med* 65, 717-721 (2017).
Lunding et al., IL-37 requires IL-18Ralpha and SIGIRR/IL-1R8 to diminish allergic airway inflammation in mice. *Allergy* 70, 366-373 (2015).
Luo et al., Intracellular TL-37b interacts with Smad3 to suppress multiple signaling pathways and the metastatic phenotype of tumor cells. *Oncogene* 36, 2889-2899 (2017).
Lv et al., IL-37 inhibits IL-4/IL-13-induced CCL11 production and lung eosinophilia in murine allergic asthma. *Allergy* 73, 1642-1652 (2018).
Mahakur et al., Allo-specific immune response profiles indicative of acute rejection in kidney allografts using an in vitro lymphocyte culture-based model. *Clin Exp Nephrol* 22, 465-473 (2018).
Marchetti et al., OLT1177, a beta-sulfonyl nitrile compound, safe in humans, inhibits the NLRP3 inflammasome and reverses the metabolic cost of inflammation. *Proc Natl Acad Sci U S A* 115, E1530-E1539 (2018).
Marchetti et al., Supplement, "OLT1177, a beta-sulfonyl nitrile compound, safe in humans, inhibits the NLRP3 inflammasome and reverses the metabolic cost of inflammation", 2018, *Proc Natl Acad Sci*, 115(7), 21 pages.
Mastrangelo et al., Low-grade chronic inflammation mediated by mast cells in fibromyalgia: role of IL-37, *J Biol Regul Homeost Agents* 32, 195-198 (2018).
McCurdy et al., Macrophage-Specific Expression of IL-37 in Hyperlipidemic Mice Attenuates Atherosclerosis. *J Immunol* 199, 3604-3613 (2017).
McCurdy et al., Potential role of TL-37 in atherosclerosis. *Cytokine* 122, 154169 (2019).
Montanari et al., Interleukin-33 stimulates GM-CSF and M-CSF production by human endothelial cells. *Thromb Haemost* 116, 317-327 (2016).
Mookherjee et al., Evaluation of the IL1 Gene Cluster Single Nucleotide Polymorphisms in Primary Open-Angle Glaucoma Pathogenesis. *Genet Test Mol Biomarkers* 20, 633-636 (2016).
Nold et al., IL-37 is a fundamental inhibitor of innate immunity. *Nat Immunol* 11, 1014-1022 (2010).
Offenbacher et al., GWAS for Interleukin-1beta levels in gingival crevicular fluid identifies IL37 variants in periodontal inflammation. *Nat Commun* 9, 3686 (2018).
Pan et al., IL-1H, an interleukin 1-related protein that binds IL-18 receptor/IL-1Rrp. *Cytokine* 13, 1-7 (2001).
Pulaski et al., Mouse 4T1 breast tumor model. *Curr Protoc Immunol* Chapter 20, Unit 20 22 (2001).
R&D Systems, Recombinant Human IL-37/IL-1F7, Product Data Sheet (Catalog No. 1975-IL), available online at https://resources.rndsystems.com/pdfs/datasheets/1975-il.pdf?v=20210314 (Last Accessed Mar. 14, 2021).
R&D Systems, Recombinant Human IL-37/IL-1F7, Product Data Sheet (Catalog No. 9225-IL), available online at https://resources.rndsystems.com/pdfs/datasheets/9225-il.pdf?v=20210314 (Last Accessed Mar. 14, 2021).
R&D Systems, Recombinant Human IL-37b/IL-1F7b (aa 46-218), Product Data Sheet (Catalog No. 7585-IL), available online at https://resources.rndsystems.com/pdfs/datasheets/7585-il.pdf?v=20210404 (Last Accessed Apr. 4, 2021).

Robuffo et al., Mast cell in innate immunity mediated by proinflammatory and antiinflammatory IL-1 family members. *J Biol Regul Homeost Agents* 31, 837-842 (2017).
Rudloff et al., Monocytes and dendritic cells are the primary sources of interleukin 37 in human immune cells. *J Leukoc Biol* 101, 901-911 (2017).
Saeed et al., TL-37 inhibits lipopolysaccharide-induced osteoclast formation and bone resorption in vivo. *Immunol Lett* 175, 8-15 (2016).
Sarhan et al., Adaptive NK Cells Resist Regulatory T-cell Suppression Driven by IL37. *Cancer Immunol Res* 6, 766-775 (2018).
Schauer et al., IL-37 Causes Excessive Inflammation and Tissue Damage in Murine Pneumococcal Pneumonia. *J Innate Immun* 9, 403-418 (2017).
Shen et al., Decreased expression of interleukin37 and its antiinflammatory effect in allergic rhinitis. *Mol Med Rep* 17, 1333-1339 (2018).
Shou et al., Plasma IL-37 Elevated in Patients with Chronic Heart Failure and Predicted Major Adverse Cardiac Events: A 1-Year Follow-Up Study. *Dis Markers* 2017, 9134079 (2017).
Tan et al., Genetic analysis of innate immunity in Behcet's disease identifies an association with IL-37 and IL-18RAP, *Sci Rep* 6, 35802 (2016).
Tawfik et al., Serum Interleukin-37: a new player in Lupus Nephritis? *Int J Rheum Dis* 20, 996-1001 (2017).
Toniato et al., Activation and inhibition of adaptive immune response mediated by mast cells. *J Biol Regul Homeost Agents* 31, 543-548 (2017).
Trajano et al. Endotoxin-induced acute lung injury is dependent upon oxidative response. *Inhalation Toxicology* 23, 918-926 (2011).
Van Geffen et al., IL37 dampens the IL1beta-induced catabolic status of human OA chondrocytes. *Rheumatology (Oxford)* 56, 351-361 (2017).
Wang et al., Interleukin-37 Enhances the Suppressive Activity of Naturally Occurring CD4(+)CD25(+) Regulatory T Cells. *Sci Rep* 6, 38955 (2016).
Wang et al., Transfer of the IL-37b gene elicits anti-tumor responses in mice bearing 4T1 breast cancer. *Acta Pharmacol Sin* 36, 528-534 (2015).
Wu et al., Elevated plasma interleukin-37 levels in systemic lupus erythematosus patients. *Lupus* 25, 1377-1380 (2016).
Xie, et al., Interleukin-37 suppresses ICAM-1 expression in parallel with NF-kappaB down-regulation following TLR2 activation of human coronary artery endothelial cells. *Int Immunopharmacol* 38, 26-30 (2016).
Xu et al., Insights into IL-37, the role in autoimmune diseases. *Autoimmun Rev* 14, 1170-1175 (2015).
Yan et al., Common genetic heterogeneity of human interleukin-37 leads to functional variance. *Cell Mol Immunol* 14, 783-791 (2017).
Yan et al., Interleukin-37 mediates the antitumor activity in colon cancer through beta-catenin suppression, *Oncotarget* 8, 49064-49075 (2017).
Yang et al., Elevated plasma interleukin-37 playing an important role in acute coronary syndrome through suppression of ROCK activation. *Oncotarget* 8, 9686-9695 (2017).
Yin et al., Genomic Variant in IL-37 Confers A Significant Risk of Coronary Artery Disease. *Sci Rep* 7, 42175 (2017).
Yu et al., Increased IL-37 concentrations in patients with arterial calcification. *Clin Chim Acta* 461, 19-24 (2016).
Yu et al., IL-37 and 38 signalling in gestational diabetes. *J Reprod Immunol* 124, 8-14 (2017).
Zeinali et al., Inflammatory and anti-inflammatory cytokines in the seminal plasma of infertile men suffering from varicocele. *Andrologia* 49, e12685 (2017).
Zeng et al., Interleukin-37 suppresses the osteogenic responses of human aortic valve interstitial cells in vitro and alleviates valve lesions in mice. *Proc Natl Acad Sci U S A* 114, 1631-1636 (2017).
Zhang et al., Gastrodin protects against LPS-induced acute lung injury by activating Nrf2 signaling pathway. *Oncotarget* 8, 32147-32156 (2017).
Zhang et al., Tuberculosis-sensitized monocytes sustain immune response of interleukin-37. *Mol Immunol* 79, 14-21 (2016).

(56) References Cited

OTHER PUBLICATIONS

Zhang et al., The potential of interleukin-37 as an effective therapeutic agent in asthma. *Respir Res* 18, 192 (2017).
Zhang et al., IL1F7 Gene Polymorphism is Not Associated with Rheumatoid Arthritis Susceptibility in the Northern Chinese Han Population: A Case-Control Study. *Chin Med J (Engl)* 131, 171-179 (2018).
Zhao et al., Interleukin-37 mediates the antitumor activity in hepatocellular carcinoma: role for CD57+ NK cells. *Sci Rep* 4, 5177 (2014).
Zhao et al., TL-37 impairs host resistance to Listeria infection by suppressing macrophage function. *Biochem Biophys Res Commun* 485, 563-568 (2017).
Zhao et al., Involvement of IL-37 in the Pathogenesis of Proliferative Diabetic Retinopathy. *Invest Ophthalmol Vis Sci* 57, 2955-2962 (2016).
Zhu et al., Interleukin-37 and Dendritic Cells Treated With Interleukin-37 Plus Troponin I Ameliorate Cardiac Remodeling After Myocardial Infarction. *J Am Heart Assoc* 5, (2016).
Zou et al., Acyloxyacyl hydrolase promotes the resolution of lipopolysaccharide-induced acute lung injury. *PLOS Pathog.* 13(6): e1006436 (2017).
International Search Report and Written Opinion for PCT/US18/23311, dated Jun. 4, 2018, 10 pages.
International Preliminary Report on Patentability for PCT/US18/23311, dated Sep. 24, 2019, 6 pages.

\* cited by examiner

Structure A.
| Human IL-37: Val46-Asp218 | Linker: GGGS | IgG1-Fc sequence |

Structure B.
| Human IL-37: Val46-Val206 | Linker: GGGS | human IgG1-Fc sequence |

Structure C.
| Human IL-37: Lys53-Val206 | Linker: GGGS | human IgG1-Fc sequence |

Figure 1D

| Human CD33 signal sequence | Human IL-37: Val46-Asp218 | Linker: GGGS | human IgG1-Fc sequence |

| Human CD33 signal sequence | Human IL-37: Val46-Val206 | Linker: GGGS | human IgG1-Fc sequence |

| Human CD33 signal sequence | Human IL-37: Lys53-Val206 | Linker: GGGS | human IgG1-Fc sequence |

Figure 1E

| | | | | | | | |
|---|---|---|---|---|---|---|---|
| 1 | VHTSPKVKNL | NPKKFSIHDQ | DHKVLVLDSG | NLIAVPDKNY | IRPEIFFALA | SSLSSASAEK | 60 |
| 61 | GSPILLGVSK | GEFCLYCDKD | KGQSHPSLQL | KKEKLMKLAA | QKESARRPFI | FYRAQVGSWN | 120 |
| 121 | MLESAAHPGW | FICTSCNCNE | PVGVTDKFEN | RKHIEFSFQP | VGGGSPKSCD | KTHTCPPCPA | 180 |
| 181 | PEAEGAPSVF | LFPPKPKDTL | MISRTPEVTC | VVVDVSHEDP | EVKFNWYVDG | VEVHNAKTKP | 240 |
| 241 | REEQYNSTYR | VVSVLTVLHQ | DWLNGKEYKC | KVSNKALPAP | IEKTISKAKG | QPREPQVYTL | 300 |
| 301 | PPSRDELTKN | QVSLTCLVKG | FYPSDIAVEW | ESNGQPENNY | KATPPVLDSD | GSFFLYSKLT | 360 |
| 361 | VDKSRWQQGN | VFSCSVMHEA | LHNHYTQKSL | SLSPGK | | | |

Figure 1F

| | | | | | | | |
|---|---|---|---|---|---|---|---|
| 1 | KNLNPKKFSI | HDQDHKVLVL | DSGNLIAVPD | KNYIRPEIFF | ALASSLSSAS | AEKGSPILLG | 60 |
| 61 | VSKGEFCLYC | DKDKGQSHPS | LQLKKEKLMK | LAAQKESARR | PFIFYRAQVG | SWNMLESAAH | 120 |
| 121 | PGWFICTSCN | CNEPVGVTDK | FENRKHIEFS | FQPVGGGSPK | SCDKTHTCPP | CPAPEAEGAP | 180 |
| 181 | SVFLFPPKPK | DTLMISRTPE | VTCVVVDVSH | EDPEVKFNWY | VDGVEVHNAK | TKPREEQYNS | 240 |
| 241 | TYRVVSVLTV | LHQDWLNGKE | YKCKVSNKAL | PAPIEKTISK | AKGQPREPQV | YTLPPSRDEL | 300 |
| 301 | TKNQVSLTCL | VKGFYPSDIA | VEWESNGQPE | NNYKATPPVL | DSDGSFFLYS | KLTVDKSRWQ | 360 |
| 361 | QGNVFSCSVM | HEALHNHYTQ | KSLSLSPGK | | | | 389 |

Figure 1G

MPLLLLLPLLWAGALAVHTSPKVKNLNPKKFSIHDQDHKVLVLDSGNLIAVPDKNYIRPE
IFFALASSLSSASAEKGSPILLGVSKGEFCLYCDKDKGQSHPSLQLKKEKLMKLAAQKES
ARRPFIFYRAQVGSWNMLESAAHPGWFICTSCNCNEPVGVTDKFENRKHIEFSFQPVGGGS
PKSCDKTHTCPPCPAPEAEGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKATP
PVLDSDGSFFLYSKLTVDKSRWQQGNVFSCSVMHEALHNHYTQKSLSLSPGK

IL-1β levels in whole lung homogenates following poly I:C

SEQUENCE LISTING

<160> NUMBER OF SEQ ID NOS: 15

<210> SEQ ID NO 1
<211> LENGTH: 173
<212> TYPE: PRT
<213> ORGANISM: Homo sapiens

<400> SEQUENCE: 1

```
Val His Thr Ser Pro Lys Val Lys Asn Leu Asn Pro Lys Lys Phe Ser
1               5                   10                  15

Ile His Asp Gln Asp His Lys Val Leu Val Leu Asp Ser Gly Asn Leu
            20                  25                  30

Ile Ala Val Pro Asp Lys Asn Tyr Ile Arg Pro Glu Ile Phe Phe Ala
        35                  40                  45

Leu Ala Ser Ser Leu Ser Ser Ala Ser Ala Glu Lys Gly Ser Pro Ile
    50                  55                  60

Leu Leu Gly Val Ser Lys Gly Glu Phe Cys Leu Tyr Cys Asp Lys Asp
65                  70                  75                  80

Lys Gly Gln Ser His Pro Ser Leu Gln Leu Lys Lys Glu Lys Leu Met
                85                  90                  95

Lys Leu Ala Ala Gln Lys Glu Ser Ala Arg Arg Pro Phe Ile Phe Tyr
            100                 105                 110

Arg Ala Gln Val Gly Ser Trp Asn Met Leu Glu Ser Ala Ala His Pro
        115                 120                 125

Gly Trp Phe Ile Cys Thr Ser Cys Asn Cys Asn Glu Pro Val Gly Val
    130                 135                 140

Thr Asp Lys Phe Glu Asn Arg Lys His Ile Glu Phe Ser Phe Gln Pro
145                 150                 155                 160
```

```
Val Cys Lys Ala Glu Met Ser Pro Ser Glu Val Ser Asp
                165                 170
```

<210> SEQ ID NO 2
<211> LENGTH: 161
<212> TYPE: PRT
<213> ORGANISM: Homo sapiens

<400> SEQUENCE: 2

```
Val His Thr Ser Pro Lys Val Lys Asn Leu Asn Pro Lys Lys Phe Ser
1               5                   10                  15

Ile His Asp Gln Asp His Lys Val Leu Val Leu Asp Ser Gly Asn Leu
            20                  25                  30

Ile Ala Val Pro Asp Lys Asn Tyr Ile Arg Pro Glu Ile Phe Phe Ala
        35                  40                  45

Leu Ala Ser Ser Leu Ser Ser Ala Ser Ala Glu Lys Gly Ser Pro Ile
    50                  55                  60

Leu Leu Gly Val Ser Lys Gly Glu Phe Cys Leu Tyr Cys Asp Lys Asp
65                  70                  75                  80

Lys Gly Gln Ser His Pro Ser Leu Gln Leu Lys Lys Glu Lys Leu Met
                85                  90                  95

Lys Leu Ala Ala Gln Lys Glu Ser Ala Arg Arg Pro Phe Ile Phe Tyr
            100                 105                 110

Arg Ala Gln Val Gly Ser Trp Asn Met Leu Glu Ser Ala Ala His Pro
        115                 120                 125

Gly Trp Phe Ile Cys Thr Ser Cys Asn Cys Asn Glu Pro Val Gly Val
    130                 135                 140

Thr Asp Lys Phe Glu Asn Arg Lys His Ile Glu Phe Ser Phe Gln Pro
145                 150                 155                 160

Val
```

<210> SEQ ID NO 3
<211> LENGTH: 154
<212> TYPE: PRT
<213> ORGANISM: Homo sapiens

<400> SEQUENCE: 3

```
Lys Asn Leu Asn Pro Lys Lys Phe Ser Ile His Asp Gln Asp His Lys
1               5                   10                  15

Val Leu Val Leu Asp Ser Gly Asn Leu Ile Ala Val Pro Asp Lys Asn
            20                  25                  30

Tyr Ile Arg Pro Glu Ile Phe Phe Ala Leu Ala Ser Ser Leu Ser Ser
        35                  40                  45

Ala Ser Ala Glu Lys Gly Ser Pro Ile Leu Leu Gly Val Ser Lys Gly
    50                  55                  60

Glu Phe Cys Leu Tyr Cys Asp Lys Asp Lys Gly Gln Ser His Pro Ser
65                  70                  75                  80

Leu Gln Leu Lys Lys Glu Lys Leu Met Lys Leu Ala Ala Gln Lys Glu
                85                  90                  95

Ser Ala Arg Arg Pro Phe Ile Phe Tyr Arg Ala Gln Val Gly Ser Trp
            100                 105                 110

Asn Met Leu Glu Ser Ala Ala His Pro Gly Trp Phe Ile Cys Thr Ser
        115                 120                 125

Cys Asn Cys Asn Glu Pro Val Gly Val Thr Asp Lys Phe Glu Asn Arg
    130                 135                 140

Lys His Ile Glu Phe Ser Phe Gln Pro Val
                145                 150
```

<210> SEQ ID NO 4
<211> LENGTH: 231
<212> TYPE: PRT
<213> ORGANISM: Homo sapiens

<400> SEQUENCE: 4

```
Pro Lys Ser Cys Asp Lys Thr His Thr Cys Pro Pro Cys Pro Ala Pro
1               5                   10                  15

Glu Ala Glu Gly Ala Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Ala Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 5
<211> LENGTH: 231
<212> TYPE: PRT
<213> ORGANISM: artificial
<220> FEATURE:
<223> OTHER INFORMATION: non-lytic hIgG1-Fc sequence

<400> SEQUENCE: 5

```
Pro Lys Ser Cys Asp Lys Thr His Thr Cys Pro Pro Cys Pro Ala Pro
1               5                   10                  15

Glu Ala Glu Gly Ala Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80
```

```
Asn Ser Thr Tyr Arg Val Val Ser Val Leu Thr Val Leu His Gln Asp
                85                  90                  95

Trp Leu Asn Gly Lys Ala Tyr Ala Cys Ala Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Ala Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 6
<211> LENGTH: 16
<212> TYPE: PRT
<213> ORGANISM: artificial
<220> FEATURE:
<223> OTHER INFORMATION: CD33 signal sequence

<400> SEQUENCE: 6

Met Pro Leu Leu Leu Leu Leu Pro Leu Leu Trp Ala Gly Ala Leu Ala
1               5                   10                  15

<210> SEQ ID NO 7
<211> LENGTH: 396
<212> TYPE: PRT
<213> ORGANISM: artificial
<220> FEATURE:
<223> OTHER INFORMATION: human IL-37 Fc aa46-206

<400> SEQUENCE: 7

Val His Thr Ser Pro Lys Val Lys Asn Leu Asn Pro Lys Lys Phe Ser
1               5                   10                  15

Ile His Asp Gln Asp His Lys Val Leu Val Leu Asp Ser Gly Asn Leu
                20                  25                  30

Ile Ala Val Pro Asp Lys Asn Tyr Ile Arg Pro Glu Ile Phe Phe Ala
            35                  40                  45

Leu Ala Ser Ser Leu Ser Ser Ala Ser Ala Glu Lys Gly Ser Pro Ile
        50                  55                  60

Leu Leu Gly Val Ser Lys Gly Glu Phe Cys Leu Tyr Cys Asp Lys Asp
65                  70                  75                  80

Lys Gly Gln Ser His Pro Ser Leu Gln Leu Lys Glu Lys Leu Met
                85                  90                  95

Lys Leu Ala Ala Gln Lys Glu Ser Ala Arg Arg Pro Phe Ile Phe Tyr
            100                 105                 110

Arg Ala Gln Val Gly Ser Trp Asn Met Leu Glu Ser Ala Ala His Pro
        115                 120                 125

Gly Trp Phe Ile Cys Thr Ser Cys Asn Cys Asn Glu Pro Val Gly Val
```

```
                130             135             140
Thr Asp Lys Phe Glu Asn Arg Lys His Ile Glu Phe Ser Phe Gln Pro
145                 150                 155                 160

Val Gly Gly Gly Ser Pro Lys Ser Cys Asp Lys Thr His Thr Cys Pro
                165                 170                 175

Pro Cys Pro Ala Pro Glu Ala Glu Gly Ala Pro Ser Val Phe Leu Phe
            180                 185                 190

Pro Pro Lys Pro Lys Asp Thr Leu Met Ile Ser Arg Thr Pro Glu Val
                195                 200                 205

Thr Cys Val Val Val Asp Val Ser His Glu Asp Pro Glu Val Lys Phe
210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
                260                 265                 270

Ser Asn Lys Ala Leu Pro Ala Pro Ile Glu Lys Thr Ile Ser Lys Ala
            275                 280                 285

Lys Gly Gln Pro Arg Glu Pro Gln Val Tyr Thr Leu Pro Pro Ser Arg
290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Ala Thr Pro Pro Val Leu Asp Ser Asp Gly Ser
                340                 345                 350

Phe Phe Leu Tyr Ser Lys Leu Thr Val Asp Lys Ser Arg Trp Gln Gln
                355                 360                 365

Gly Asn Val Phe Ser Cys Ser Val Met His Glu Ala Leu His Asn His
                370                 375                 380

Tyr Thr Gln Lys Ser Leu Ser Leu Ser Pro Gly Lys
385                 390                 395

<210> SEQ ID NO 8
<211> LENGTH: 389
<212> TYPE: PRT
<213> ORGANISM: artificial
<220> FEATURE:
<223> OTHER INFORMATION: human IL-37 Fc aa53-206

<400> SEQUENCE: 8

Lys Asn Leu Asn Pro Lys Lys Phe Ser Ile His Asp Gln Asp His Lys
1               5                   10                  15

Val Leu Val Leu Asp Ser Gly Asn Leu Ile Ala Val Pro Asp Lys Asn
                20                  25                  30

Tyr Ile Arg Pro Glu Ile Phe Phe Ala Leu Ala Ser Ser Leu Ser Ser
            35                  40                  45

Ala Ser Ala Glu Lys Gly Ser Pro Ile Leu Leu Gly Val Ser Lys Gly
50                  55                  60

Glu Phe Cys Leu Tyr Cys Asp Lys Asp Lys Gly Gln Ser His Pro Ser
65                  70                  75                  80

Leu Gln Leu Lys Lys Glu Lys Leu Met Lys Leu Ala Ala Gln Lys Glu
                85                  90                  95

Ser Ala Arg Arg Pro Phe Ile Phe Tyr Arg Ala Gln Val Gly Ser Trp
```

```
            100                 105                 110
Asn Met Leu Glu Ser Ala Ala His Pro Gly Trp Phe Ile Cys Thr Ser
        115                 120                 125

Cys Asn Cys Asn Glu Pro Val Gly Val Thr Asp Lys Phe Glu Asn Arg
130                 135                 140

Lys His Ile Glu Phe Ser Phe Gln Pro Val Gly Gly Ser Pro Lys
145                 150                 155                 160

Ser Cys Asp Lys Thr His Thr Cys Pro Pro Cys Pro Ala Pro Glu Ala
                165                 170                 175

Glu Gly Ala Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
        195                 200                 205

Ser His Glu Asp Pro Glu Val Lys Phe Asn Trp Tyr Val Asp Gly Val
    210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
        275                 280                 285

Gln Val Tyr Thr Leu Pro Pro Ser Arg Asp Glu Leu Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Ala Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
    370                 375                 380

Leu Ser Pro Gly Lys
385

<210> SEQ ID NO 9
<211> LENGTH: 192
<212> TYPE: PRT
<213> ORGANISM: Homo sapiens

<400> SEQUENCE: 9

Met Ser Gly Cys Asp Arg Arg Glu Thr Glu Thr Lys Gly Lys Asn Ser
1               5                   10                  15

Phe Lys Lys Arg Leu Arg Gly Pro Lys Val Lys Asn Leu Asn Pro Lys
            20                  25                  30

Lys Phe Ser Ile His Asp Gln Asp His Lys Val Leu Val Leu Asp Ser
        35                  40                  45

Gly Asn Leu Ile Ala Val Pro Asp Lys Asn Tyr Ile Arg Pro Glu Ile
    50                  55                  60

Phe Phe Ala Leu Ala Ser Ser Leu Ser Ser Ala Ser Ala Glu Lys Gly
65                  70                  75                  80
```

```
Ser Pro Ile Leu Leu Gly Val Ser Lys Gly Glu Phe Cys Leu Tyr Cys
                85                  90                  95

Asp Lys Asp Lys Gly Gln Ser His Pro Ser Leu Gln Leu Lys Lys Glu
            100                 105                 110

Lys Leu Met Lys Leu Ala Ala Gln Lys Glu Ser Ala Arg Arg Pro Phe
            115                 120                 125

Ile Phe Tyr Arg Ala Gln Val Gly Ser Trp Asn Met Leu Glu Ser Ala
            130                 135                 140

Ala His Pro Gly Trp Phe Ile Cys Thr Ser Cys Asn Cys Asn Glu Pro
145                 150                 155                 160

Val Gly Val Thr Asp Lys Phe Glu Asn Arg Lys His Ile Glu Phe Ser
            165                 170                 175

Phe Gln Pro Val Cys Lys Ala Glu Met Ser Pro Ser Glu Val Ser Asp
            180                 185                 190
```

<210> SEQ ID NO 10
<211> LENGTH: 218
<212> TYPE: PRT
<213> ORGANISM: Homo sapiens

<400> SEQUENCE: 10

```
Met Ser Phe Val Gly Glu Asn Ser Gly Val Lys Met Gly Ser Glu Asp
1               5                   10                  15

Trp Glu Lys Asp Glu Pro Gln Cys Cys Leu Glu Asp Pro Ala Gly Ser
            20                  25                  30

Pro Leu Glu Pro Gly Pro Ser Leu Pro Thr Met Asn Phe Val His Thr
            35                  40                  45

Ser Pro Lys Val Lys Asn Leu Asn Pro Lys Lys Phe Ser Ile His Asp
50                  55                  60

Gln Asp His Lys Val Leu Val Leu Asp Ser Gly Asn Leu Ile Ala Val
65                  70                  75                  80

Pro Asp Lys Asn Tyr Ile Arg Pro Glu Ile Phe Phe Ala Leu Ala Ser
            85                  90                  95

Ser Leu Ser Ser Ala Ser Ala Glu Lys Gly Ser Pro Ile Leu Leu Gly
            100                 105                 110

Val Ser Lys Gly Glu Phe Cys Leu Tyr Cys Asp Lys Asp Lys Gly Gln
            115                 120                 125

Ser His Pro Ser Leu Gln Leu Lys Lys Glu Lys Leu Met Lys Leu Ala
            130                 135                 140

Ala Gln Lys Glu Ser Ala Arg Arg Pro Phe Ile Phe Tyr Arg Ala Gln
145                 150                 155                 160

Val Gly Ser Trp Asn Met Leu Glu Ser Ala Ala His Pro Gly Trp Phe
            165                 170                 175

Ile Cys Thr Ser Cys Asn Cys Asn Glu Pro Val Gly Val Thr Asp Lys
            180                 185                 190

Phe Glu Asn Arg Lys His Ile Glu Phe Ser Phe Gln Pro Val Cys Lys
            195                 200                 205

Ala Glu Met Ser Pro Ser Glu Val Ser Asp
210                 215
```

<210> SEQ ID NO 11
<211> LENGTH: 178
<212> TYPE: PRT
<213> ORGANISM: Homo sapiens

<400> SEQUENCE: 11

```
Met Ser Phe Val Gly Glu Asn Ser Gly Val Lys Met Gly Ser Glu Asp
1               5                   10                  15

Trp Glu Lys Asp Glu Pro Gln Cys Cys Leu Glu Asp Pro Ala Gly Ser
                20                  25                  30

Pro Leu Glu Pro Gly Pro Ser Leu Pro Thr Met Asn Phe Val His Thr
            35                  40                  45

Glu Ile Phe Phe Ala Leu Ala Ser Ser Leu Ser Ser Ala Ser Ala Glu
50                  55                  60

Lys Gly Ser Pro Ile Leu Leu Gly Val Ser Lys Gly Glu Phe Cys Leu
65                  70                  75                  80

Tyr Cys Asp Lys Asp Lys Gly Gln Ser His Pro Ser Leu Gln Leu Lys
                85                  90                  95

Lys Glu Lys Leu Met Lys Leu Ala Ala Gln Lys Glu Ser Ala Arg Arg
            100                 105                 110

Pro Phe Ile Phe Tyr Arg Ala Gln Val Gly Ser Trp Asn Met Leu Glu
            115                 120                 125

Ser Ala Ala His Pro Gly Trp Phe Ile Cys Thr Ser Cys Asn Cys Asn
            130                 135                 140

Glu Pro Val Gly Val Thr Asp Lys Phe Glu Asn Arg Lys His Ile Glu
145                 150                 155                 160

Phe Ser Phe Gln Pro Val Cys Lys Ala Glu Met Ser Pro Ser Glu Val
                165                 170                 175

Ser Asp

<210> SEQ ID NO 12
<211> LENGTH: 197
<212> TYPE: PRT
<213> ORGANISM: Homo sapiens

<400> SEQUENCE: 12

Met Ser Phe Val Gly Glu Asn Ser Gly Val Lys Met Gly Ser Glu Asp
1               5                   10                  15

Trp Glu Lys Asp Glu Pro Gln Cys Cys Leu Glu Gly Pro Lys Val Lys
                20                  25                  30

Asn Leu Asn Pro Lys Lys Phe Ser Ile His Asp Gln Asp His Lys Val
            35                  40                  45

Leu Val Leu Asp Ser Gly Asn Leu Ile Ala Val Pro Asp Lys Asn Tyr
50                  55                  60

Ile Arg Pro Glu Ile Phe Phe Ala Leu Ala Ser Ser Leu Ser Ser Ala
65                  70                  75                  80

Ser Ala Glu Lys Gly Ser Pro Ile Leu Leu Gly Val Ser Lys Gly Glu
                85                  90                  95

Phe Cys Leu Tyr Cys Asp Lys Asp Lys Gly Gln Ser His Pro Ser Leu
            100                 105                 110

Gln Leu Lys Lys Glu Lys Leu Met Lys Leu Ala Ala Gln Lys Glu Ser
            115                 120                 125

Ala Arg Arg Pro Phe Ile Phe Tyr Arg Ala Gln Val Gly Ser Trp Asn
            130                 135                 140

Met Leu Glu Ser Ala Ala His Pro Gly Trp Phe Ile Cys Thr Ser Cys
145                 150                 155                 160

Asn Cys Asn Glu Pro Val Gly Val Thr Asp Lys Phe Glu Asn Arg Lys
                165                 170                 175

His Ile Glu Phe Ser Phe Gln Pro Val Cys Lys Ala Glu Met Ser Pro
            180                 185                 190
```

Ser Glu Val Ser Asp
        195

<210> SEQ ID NO 13
<211> LENGTH: 157
<212> TYPE: PRT
<213> ORGANISM: Homo sapiens

<400> SEQUENCE: 13

Met Ser Phe Val Gly Glu Asn Ser Gly Val Lys Met Gly Ser Glu Asp
1               5                   10                  15

Trp Glu Lys Asp Glu Pro Gln Cys Cys Leu Glu Glu Ile Phe Phe Ala
            20                  25                  30

Leu Ala Ser Ser Leu Ser Ser Ala Ser Ala Glu Lys Gly Ser Pro Ile
        35                  40                  45

Leu Leu Gly Val Ser Lys Gly Glu Phe Cys Leu Tyr Cys Asp Lys Asp
    50                  55                  60

Lys Gly Gln Ser His Pro Ser Leu Gln Leu Lys Lys Glu Lys Leu Met
65                  70                  75                  80

Lys Leu Ala Ala Gln Lys Glu Ser Ala Arg Arg Pro Phe Ile Phe Tyr
                85                  90                  95

Arg Ala Gln Val Gly Ser Trp Asn Met Leu Glu Ser Ala Ala His Pro
            100                 105                 110

Gly Trp Phe Ile Cys Thr Ser Cys Asn Cys Asn Glu Pro Val Gly Val
        115                 120                 125

Thr Asp Lys Phe Glu Asn Arg Lys His Ile Glu Phe Ser Phe Gln Pro
    130                 135                 140

Val Cys Lys Ala Glu Met Ser Pro Ser Glu Val Ser Asp
145                 150                 155

<210> SEQ ID NO 14
<211> LENGTH: 412
<212> TYPE: PRT
<213> ORGANISM: artificial
<220> FEATURE:
<223> OTHER INFORMATION: CD33 signal sequence and human IL-37 Fc
      aa46-206

<400> SEQUENCE: 14

Met Pro Leu Leu Leu Leu Pro Leu Leu Trp Ala Gly Ala Leu Ala
1               5                   10                  15

Val His Thr Ser Pro Lys Val Lys Asn Leu Asn Pro Lys Lys Phe Ser
            20                  25                  30

Ile His Asp Gln Asp His Lys Val Leu Val Leu Asp Ser Gly Asn Leu
        35                  40                  45

Ile Ala Val Pro Asp Lys Asn Tyr Ile Arg Pro Glu Ile Phe Phe Ala
    50                  55                  60

Leu Ala Ser Ser Leu Ser Ser Ala Ser Ala Glu Lys Gly Ser Pro Ile
65                  70                  75                  80

Leu Leu Gly Val Ser Lys Gly Glu Phe Cys Leu Tyr Cys Asp Lys Asp
                85                  90                  95

Lys Gly Gln Ser His Pro Ser Leu Gln Leu Lys Lys Glu Lys Leu Met
            100                 105                 110

Lys Leu Ala Ala Gln Lys Glu Ser Ala Arg Arg Pro Phe Ile Phe Tyr
        115                 120                 125

Arg Ala Gln Val Gly Ser Trp Asn Met Leu Glu Ser Ala Ala His Pro
    130                 135                 140

```
Gly Trp Phe Ile Cys Thr Ser Cys Asn Cys Asn Glu Pro Val Gly Val
145                 150                 155                 160

Thr Asp Lys Phe Glu Asn Arg Lys His Ile Glu Phe Ser Phe Gln Pro
                165                 170                 175

Val Gly Gly Gly Ser Pro Lys Ser Cys Asp Lys Thr His Thr Cys Pro
            180                 185                 190

Pro Cys Pro Ala Pro Glu Ala Glu Gly Ala Pro Ser Val Phe Leu Phe
        195                 200                 205

Pro Pro Lys Pro Lys Asp Thr Leu Met Ile Ser Arg Thr Pro Glu Val
    210                 215                 220

Thr Cys Val Val Val Asp Val Ser His Glu Asp Pro Glu Val Lys Phe
225                 230                 235                 240

Asn Trp Tyr Val Asp Gly Val Glu Val His Asn Ala Lys Thr Lys Pro
                245                 250                 255

Arg Glu Glu Gln Tyr Asn Ser Thr Tyr Arg Val Val Ser Val Leu Thr
                260                 265                 270

Val Leu His Gln Asp Trp Leu Asn Gly Lys Glu Tyr Lys Cys Lys Val
            275                 280                 285

Ser Asn Lys Ala Leu Pro Ala Pro Ile Glu Lys Thr Ile Ser Lys Ala
290                 295                 300

Lys Gly Gln Pro Arg Glu Pro Gln Val Tyr Thr Leu Pro Pro Ser Arg
305                 310                 315                 320

Asp Glu Leu Thr Lys Asn Gln Val Ser Leu Thr Cys Leu Val Lys Gly
                325                 330                 335

Phe Tyr Pro Ser Asp Ile Ala Val Glu Trp Glu Ser Asn Gly Gln Pro
            340                 345                 350

Glu Asn Asn Tyr Lys Ala Thr Pro Pro Val Leu Asp Ser Asp Gly Ser
                355                 360                 365

Phe Phe Leu Tyr Ser Lys Leu Thr Val Asp Lys Ser Arg Trp Gln Gln
        370                 375                 380

Gly Asn Val Phe Ser Cys Ser Val Met His Glu Ala Leu His Asn His
385                 390                 395                 400

Tyr Thr Gln Lys Ser Leu Ser Leu Ser Pro Gly Lys
                405                 410

<210> SEQ ID NO 15
<211> LENGTH: 4
<212> TYPE: PRT
<213> ORGANISM: artificial
<220> FEATURE:
<223> OTHER INFORMATION: linker peptide

<400> SEQUENCE: 15

Gly Gly Gly Ser
1
```

IL-37 FUSION PROTEIN AND METHODS OF MAKING AND USING SAME

CONTINUING APPLICATION DATA

This application is the § 371 U.S. National Stage of International Application No. PCT/US2018/023311, filed Mar. 20, 2018, which claims the benefit of U.S. Provisional Application Ser. No. 62/473,878, filed Mar. 20, 2017, and U.S. Provisional Application Ser. No. 62/589,760, filed Nov. 22, 2017, the disclosures of each of which are incorporated by reference herein in their entireties.

GOVERNMENT SUPPORT

This invention was made with government support under Grant No. AI015614, awarded by National Institutes of Health. The government has certain rights in the invention.

SEQUENCE LISTING

This application contains a Sequence Listing electronically submitted to the United States Patent and Trademark Office via EFS-Web as an ASCII text file entitled "0541-000002US01 ST25" having a size of 28 kilobytes and created on Nov. 18, 2021. Due to the electronic filing of the Sequence Listing, the electronically submitted Sequence Listing serves as both the paper copy required by 37 CFR § 1.821(c) and the computer readable form (CRF) required by § 1.821(e). The information contained in the Sequence Listing is incorporated by reference herein.

BACKGROUND

Interleukin 37 (IL-37) is a member of the IL-1 family. IL-37 can bind to interleukin 18 receptor (IL-18R) and to interleukin 18 binding protein (IL18BP), an inhibitory binding protein of interleukin 18 (IL-18). Five alternatively spliced transcript variants encoding distinct isoforms of IL-37 have been reported, and IL-37 has been reported to reduce innate inflammation as well as acquired immunity.

SUMMARY OF THE INVENTION

This disclosure describes IL-37 fusion proteins; methods of making IL-37 fusion proteins, including constructs used to express IL-37 fusion proteins; and methods of using IL-37 fusion proteins. In some embodiments, the IL-37 fusion protein includes amino acids 46-206 of isoform B of IL-37 and a heavy chain portion of an antibody.

In one aspect, this disclosure describes a fusion protein including a fragment of IL-37 and a heavy chain portion of an antibody. The fragment of IL-37 includes amino acids 46-206 of isoform B of IL-37. In some embodiments, the fragment of IL-37 consists of amino acids 46-206 of isoform B of IL-37.

In some embodiments, the fusion protein and/or the fragment of IL-37 includes SEQ ID NO:2. In some embodiments, the fragment of IL-37 consists of SEQ ID NO:2.

In some embodiments, the heavy chain portion of an antibody includes an IgG-Fc sequence. In some embodiments, the heavy chain portion of an antibody includes an IgG1-Fc sequence. In some embodiments, the fusion protein and/or the heavy chain portion of an antibody include SEQ ID NO:4.

In some embodiments, the fusion protein and/or the heavy chain portion of an antibody include mutations to a complement (C1q) binding site and/or to an Fc gamma receptor (FcγR) binding site. In some embodiments, the fusion protein and/or the heavy chain portion of an antibody include L234A and L235A (LALA) substitutions. In some embodiments, the fusion protein and/or the heavy chain portion of an antibody includes SEQ ID NO:5.

In some embodiments, the fusion protein includes a peptide linker. In some embodiments, the peptide linker includes the amino acid sequence GGGS (SEQ ID NO: 15). In some embodiments, the peptide linker connects the fragment of IL-37 and the heavy chain portion of an antibody.

In some embodiments, the fusion protein includes a signal peptide. A signal peptide can include, for example, a CD33 signal peptide. In some embodiments, the fusion protein and/or the signal peptide include SEQ ID NO:6.

In another aspect, this disclosure describes a method of using a fusion protein, as described herein. In some embodiments, the method includes administering an effective amount of an IL-37 fusion protein to a subject.

In a further aspect, this disclosure describes a method of making a fusion protein, as described herein.

In this disclosure, "operably linked" refers to a juxtaposition of components such that they are in a relationship permitting them to function in their intended manner. For example, in the context of a gene, "operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. In some embodiments, "operably linked" refers to the association of nucleic acid fragments in a single fragment so that the function of one is regulated by the other. For example, a promoter is operably linked with a nucleic acid fragment when it is capable of regulating the transcription of that nucleic acid fragment.

The words "preferred" and "preferably" refer to embodiments of the invention that may afford certain benefits, under certain circumstances. Other embodiments may also be preferred, however, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1B shows an alignment of the predicted amino acids sequences of the five IL-37 isoforms. The exon position is shown according to the arrangement in the gene. Positions of predicted β-strands are underlined.

Propeptide cleavage sites are marked by black arrows. The predicted caspase-1 cleavage site is located between D20 and E21 (present in isoforms b-e). Another experimentally-detected cleavage site is located between F45 and V46 (present in isoforms b and c), and a predicted, elastase cleavage site in exon 3 of IL-1F7a is positioned between L21 and R22 (arrow with question mark). Exon 3 also contains a putative, bi-partite nuclear localisation signal (NLS), spanning residues R5 to R22 (highlighted in gray). FIG. 1C shows a diagram of exemplary fusion protein constructs. GGGS linker peptide is SEQ ID NO: 15. FIG. 1D shows a diagram of vector constructs that can be used to produce the fusion proteins of FIG. 1C. Again, GGGS linker peptide is SEQ ID NO: 15. FIG. 1E shows the expressed sequence of amino acids 46-206 of isoform B of human IL-37 fused to an Fc domain (human IL-37 Fc aa46-206) (SEQ ID NO:7). The amino acid sequence of IL-37 aa 46-206 is in bold. The sequence of human IgG/Fc is doubly underlined, and the linker peptide, GGGS (SEQ ID NO: 15), is singly underlined. FIG. 1F shows the expressed sequence of amino acids 53-206 of isoform B of human IL-37 fused to an Fc domain (human IL-37 Fc aa53-206) (SEQ ID NO:8). The amino acid sequence of IL-37 aa 53-206 is in bold. The sequence of human IgG/Fc is doubly underlined, and the linker peptide, GGGS (SEQ ID NO: 15), is singly underlined. FIG. 1G shows he expressed sequence of amino acids 46-206 of isoform B of human IL-37 fused to an Fc domain and a CD33 signal sequence (SEQ ID NO:14). The sequence of CD33 signal sequence is highlighted in gray. The amino acid sequence of IL-37 aa 46-206 is in bold. The sequence of human IgG/Fc is doubly underlined, and the linker peptide, GGGS (SEQ ID NO: 15), is singly underlined.

DETAILED DESCRIPTION OF ILLUSTRATIVE EMBODIMENTS

This disclosure describes IL-37 fusion proteins; methods of making IL-37 fusion proteins, including constructs used to express IL-37 fusion proteins; and methods of using IL-37 fusion proteins. In some embodiments, these fusion proteins provide increased half-life in vivo compared to IL-37. In some embodiments, the fusion proteins described herein provide unexpectedly potent effects.

IL-37 Fusion Proteins

In some embodiments, an IL-37 fusion protein includes an IL-37 protein. An IL-37 protein can include a full-length IL-37 protein, a fragment of an IL-37 protein, an IL-37 protein isoform, or a fragment of an IL-37 protein isoform. In some embodiments, the IL-37 protein is preferably a human IL-37 protein.

Figure 1A:
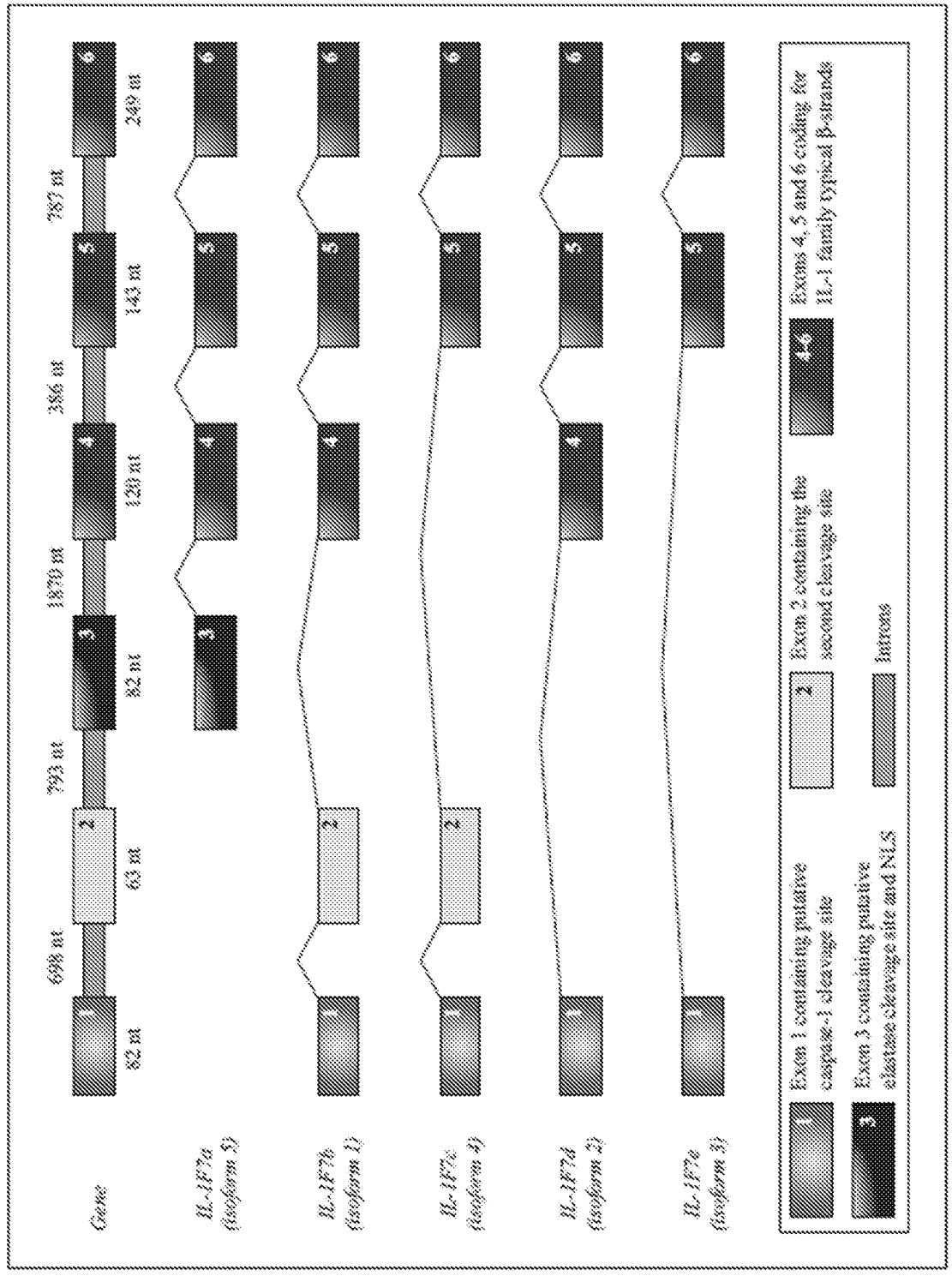
FIG. 1A shows a diagram of exon-intron structure of the human IL-37 gene. Exon usage in the five splice isoforms is depicted. The size of exons is indicated just below the exon boxes. The size of the intervening introns is shown at the top.
Figure 1B:
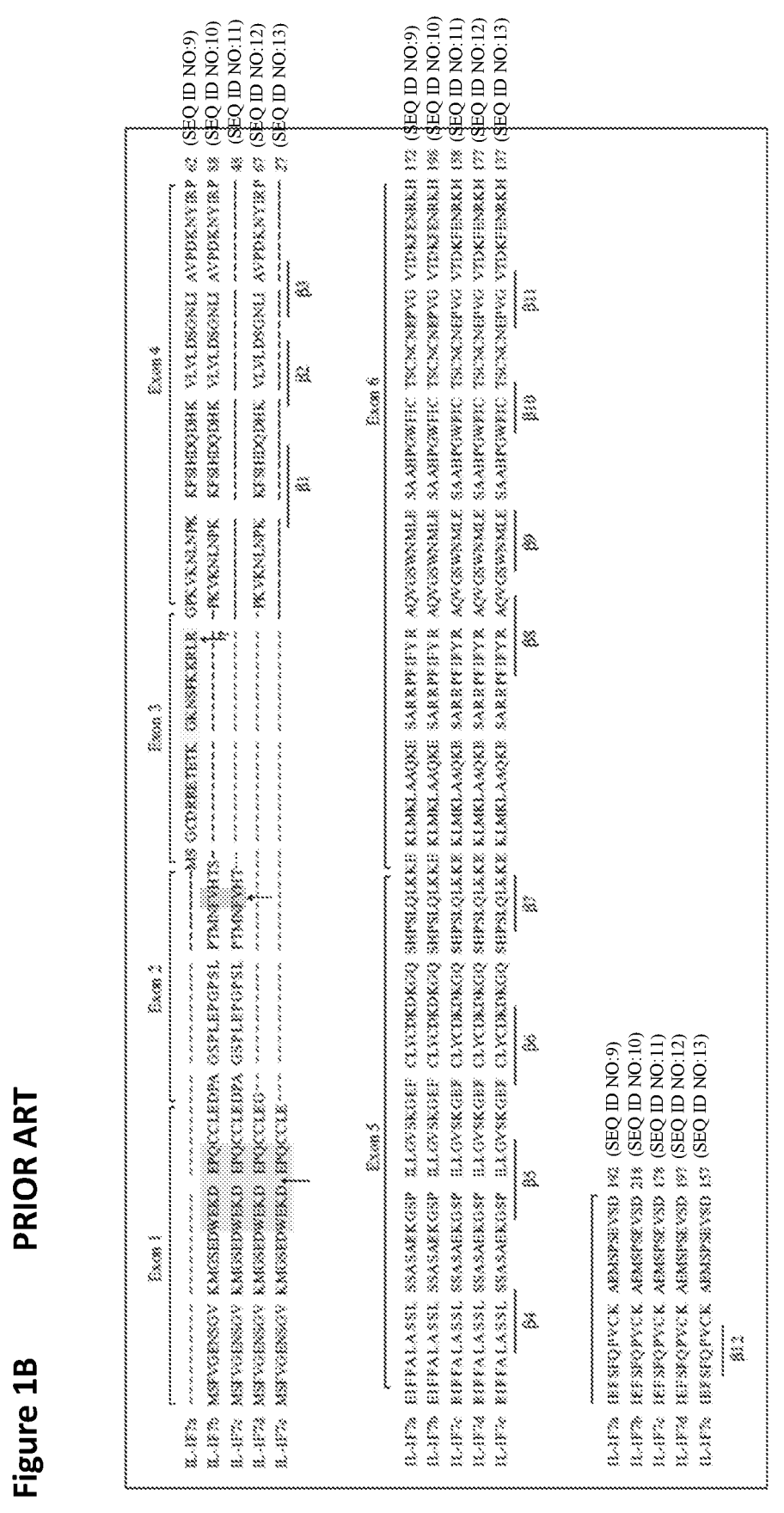

Five alternatively spliced transcript variants encoding five distinct isoforms of IL-37 have been reported. (See FIGS. 1A and 1B; Boraschi et al., Eur. Cytokine Netw. 2011, 22(3):127-147.) The expression pattern and processing of the isoforms are incompletely characterized.

Among the five isoforms of IL-37, isoform B (218 amino acids) and isoform A (192 amino acids) have domains expected to give them more potent functions.

Members of the IL-1 family tend to be processed nine amino acids prior to a three amino acid sequence characterized by an aliphatic amino acid (A), any amino acid (X), and an aspartic acid (D), known as an AXD sequence or AXD domain. The last three amino acids of IL-37 contain an AXD sequence in all isoforms. Thus, isoforms of IL-37 may be processed (cleaved) in vivo nine amino acids before the terminal AXD motif (VSD). Upon such cleaving, the C-terminus of expressed IL-37 isoform B would be Val206 and of isoform A Val155. Notably, the sequence of amino acids 53-206 of isoform B of IL-37 is identical to the sequence of amino acids 27-181 of isoform A of IL-37.

Isoform B of IL-37 also contains an AXD motif 9 amino acids after position 53, suggesting a putative N-terminus of Lys53. (See Dinarello et al. 2016, Eur. J. Immunol. 46:1067-1081.) However, at least some IL-37 expressed in mammalian cells has been sequenced and found to start at Val46 (Pan et al. 2001, Cytokine 13:1-7). The un-cleaved (unprocessed) sequence has also been detected.

In some embodiments, an IL-37 fusion protein includes a fragment of IL-37 (that is, a fragment of an IL-37 protein or a fragment of an IL-37 isoform). In some embodiments, an IL-37 fusion protein includes amino acids 46-206 of isoform B of IL-37. In some embodiments, an IL-37 fusion protein includes SEQ ID NO:2. In some embodiments, the fragment of IL-37 consists of amino acids 46-206 of isoform B of IL-37. In some embodiments, the fragment of IL-37 consists of SEQ ID NO:2.

In some embodiments, an IL-37 fusion protein includes a heavy chain portion of an antibody. In some embodiments, an IL-37 fusion protein includes an IgG-Fc sequence. In some embodiments, the IgG-Fc sequence includes an IgG1-Fc sequence, an IgG2-Fc sequence, an IgG3-Fc sequence, or an IgG4-Fc sequence. In some embodiments, the IgG1-Fc sequence can be a human IgG-Fc sequence. In some embodiments, an IL-37 fusion protein includes SEQ ID NO:4.

In some embodiments, the Fc region includes mutations to the complement (C1q) and/or to Fc gamma receptor (FcγR) binding sites. In some embodiments, such mutations can render the fusion protein incapable of antibody directed cytotoxicity (ADCC) and complement directed cytotoxicity (CDC). For example, an IgG1-Fc sequence can include L234A and L235A (LALA) substitutions, substitutions that studies have demonstrated greatly reduce binding to Fc gamma receptors (FcγRs). In some embodiments, an IL-37 fusion protein includes SEQ ID NO:5.

Fusing IL-37 to the Fc region of human IgG1 is expected to increase half-life in vivo, but the effects of an Fc region on the potency of IL-37 must be determined experimentally. As shown herein, fusion of IL-37 to the Fc region of human IgG1 and, in particular, fusion of amino acids 46-206 of isoform B of IL-37 to the Fc region of human IgG1 can produce a construct having beneficial effects on the potency of IL-37.

Surprisingly, although recombinant human IL-37 aa53-206 and recombinant human IL-37 aa46-206 exhibit near similar activities (FIG. 2), the respective fusion proteins (IL-37 Fc aa53-206 and IL-37 Fc aa46-206) do not. For example, when the fusion proteins were tested in the same types of cells at the same time, IL-37 Fc aa53-206 was observed to be less potent in suppressing IFNγ than IL-37 Fc aa46-206. Differences between the effects of the fusion proteins were also observed in other experimental models. (See, for example, FIGS. 15-16 and Examples 5-6.)

IL-37 binds to the IL-18 receptor (IL-18R). The Fc region of human IgG1 is a dimer and will, therefore, bring two IL-37 molecules into close proximity, potentially also bringing two IL-18 receptor molecules into close proximity. The effects, if any, of this proximity are unknown.

In some embodiments, an IL-37 fusion protein includes a peptide linker. In some embodiments, the peptide linker connects an IL-37 protein and an Fc sequence. In some embodiments, the peptide linker can include the amino acid sequence GGGS (SEQ ID NO: 15).

In some embodiments, an IL-37 fusion protein includes a signal peptide (sometimes referred to as a signal sequence). In some embodiments, the signal peptide can be a human signal peptide. In some embodiments, the signal peptide can include a CD33 signal peptide. In some embodiments, an IL-37 fusion protein includes SEQ ID NO:6. In some embodiments, a signal peptide can be located at the N-terminus of the IL-37 fusion protein.

Methods of Making IL-37 Fusion Proteins

This disclosure further disclosure describes methods of making an IL-37 fusion protein. In some embodiments, a sequence encoding an IL-37 protein or a fragment of IL-37 protein is fused to a sequence encoding a heavy chain portion of an antibody or a portion or a heavy chain portion of an antibody. In some embodiments, a sequence encoding an IL-37 protein or a fragment of IL-37 protein is operably linked to a sequence encoding a heavy chain portion of an antibody or a portion or a heavy chain portion of an antibody. In some embodiments, a sequence encoding a peptide linker can be included between the sequence encoding an IL-37 protein or a fragment of IL-37 and the sequence encoding a heavy chain portion of an antibody or a portion or a heavy chain portion of an antibody. In some embodiment, the sequence encoding a peptide linker can include a sequence encoding GGGS (SEQ ID NO: 15). In some embodiments, the sequence encoding an IL-37 protein or a fragment of IL-37 can be fused to a peptide encoding a signal peptide. In some embodiments, the signal peptide can include a CD33 signal sequence. In some embodiments, a sequence encoding a signal peptide is connected to and/or operably linked to a sequence encoding a fragment of IL-37.

In some embodiments, the sequence encoding the IL-37 fusion protein is inserted into a vector. In some embodiments, the vector includes a CMV promoter.

In some embodiments, a vector including a sequence encoding the IL-37 fusion protein can be introduced into a cell including, for example, by transfection. In some embodiments, the vector can be stably transfected. In some embodiments, the cell can be an HEK293 cell.

Methods of Using IL-37 Fusion Proteins

This disclosure further disclosure describes methods of using an IL-37 fusion protein. In some embodiments, the method includes administering an effective amount of an IL-37 fusion protein.

In some embodiments, a IL-37 fusion protein described herein can be used to modulate the immune system. For example, modulation of IL-37 has been shown to have a beneficial effect in, for example, subjects having a spinal cord injury (Coll-Miró et al. 2016, PNAS 113(5):1411-1416), in improvement of a subject's exercise tolerance (Cavalli et al. 2017, Proc Natl Acad Sci USA 114(9):2313-2318), in reducing joint and systemic inflammation (Cavalli et al. 2016, Rheumatology (Oxford) 55(12):2220-2229), in sickle cell anemia patients (Alagbe et al. 2017, Cytokine doi: 10.1016/j.cyto.2017.12.001), in subjects from several different experimental models of inflammation including arthritis (Cavalli et al. 2018, Immunol Rev. 281(1):179-190), human lung adenocarcinoma (Chen et al. 2017, Cancer Biomark. doi: 10.3233/CBM-170732), inflammatory bowel disease (Conti et al. 2018, Eur. J. Pharmacol. 818:294-299), osteoarthritis (Ding et al. 2017, Sci. Rep. 7:11601), alcoholic liver disease (Grabherr et al. 2017, Liver Int. doi: 10.1111/liv.13642), asthma (Huang et al. 2017, Int. Immunopharmacol. 55:198-204; Lv et al. 2018, Allergy doi: 10.1111/a11.13395), allergic rhinitis (Kim et al. 2017, Iran J. Allergy Asthma Immunology 16:404-417), atherosclerosis related diseases (Liu et al. 2018, Cell Physiol. Biochem. 45:1034-1050; McCurdy et al. 2017, J. Immunol. 199(10):3604-3613), and asthma (Zhang et al. 2017, Respir. Res. 18(1):192).

In some embodiments, a IL-37 fusion protein described herein can be administered to a subject having an IL-37 deficiency and/or low IL-37 expression levels. For example, states in which low IL-37 expression levels have been observed include obesity-induced inflammation and insulin resistance (Ballak et al. 2014, Nat. Commun. 5:4711), allergic airway inflammation and/or asthma (Lunding et al. 2015, Allergy 70(4):366-373), plaque psoriasis (Xu et al. 2015, Autoimmun. Rev. 14:1170-1175), calcific aortic valve disease (Zeng et al. 2017, PNAS USA 1114:1631-1636), and alcoholic liver disease (Grabherr et al. 2017, Liver Int. doi: 10.1111/liv.13642).

Pharmaceutical Composition

The present disclosure further provides a pharmaceutical composition that includes an IL-37 fusion protein and a pharmaceutically acceptable carrier. The IL-37 fusion protein is formulated in a pharmaceutical composition and then, in accordance with the method of the invention, administered to a vertebrate, particularly a mammal, such as a human patient, companion animal, or domesticated animal, in a variety of forms adapted to the chosen route of administration. The formulations include those suitable for oral, rectal, vaginal, topical, nasal, ophthalmic, or parenteral (including subcutaneous, intramuscular, intraperitoneal, and intravenous) administration.

The pharmaceutically acceptable carrier can include, for example, an excipient, a diluent, a solvent, an accessory ingredient, a stabilizer, a protein carrier, or a biological compound. Non-limiting examples of a protein carrier includes keyhole limpet hemocyanin (KLH), bovine serum albumin (BSA), ovalbumin, or the like. Non-limiting examples of a biological compound which can serve as a carrier include a glycosaminoglycan, a proteoglycan, and albumin. The carrier can be a synthetic compound, such as dimethyl sulfoxide or a synthetic polymer, such as a polyalkyleneglycol. Ovalbumin, human serum albumin, other proteins, polyethylene glycol, or the like can be employed as the carrier. In a preferred embodiment, the pharmaceutically acceptable carrier includes at least one compound that is not naturally occurring or a product of nature.

In some embodiments, the IL-37 fusion protein is formulated in combination with one or more additional active agents. Any known therapeutic agent can be included as an additional active agent. The action of the additional active agent in the combination therapy can be cumulative to the IL-37 fusion protein or it can be complementary, for example to manage side effects or other aspects of the patient's medical condition. In one embodiment, the combination therapy includes at least one compound that is not naturally occurring or a product of nature.

The formulations can be conveniently presented in unit dosage form and can be prepared by any of the methods well-known in the art of pharmacy. In some embodiments, a method includes the step of bringing the active agent into association with a pharmaceutical carrier. In general, the formulations are prepared by uniformly and intimately bringing the active compound into association with a liquid carrier, a finely divided solid carrier, or both, and then, if necessary, shaping the product into the desired formulations.

Formulations of the present disclosure suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into preparations and devices in formulations that may or may not be designed for sustained release.

Formulations suitable for parenteral administration conveniently include a sterile aqueous preparation of the active agent, or dispersions of sterile powders of the active agent, which are preferably isotonic with the blood of the recipient. Parenteral administration of an IL-37 fusion protein (e. g., through an I.V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, or glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration can be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations. Topical formulations can be provided in the form of a bandage, wherein the formulation is incorporated into a gauze or other structure and brought into contact with the skin.

Administration

An IL-37 fusion protein can be administered to a subject alone or in a pharmaceutical composition that includes a pharmaceutically acceptable carrier. The active agent is administered to a vertebrate, more preferably a mammal, such as a human patient, a companion animal, or a domesticated animal, in an amount effective to produce the desired effect. An IL-37 fusion protein can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

The formulations can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

Dosage levels of the active agent in the pharmaceutical compositions of this disclosure can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the IL-37 fusion protein, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician could start doses of the IL-37 fusion protein employed in the pharmaceutical composition at levels lower than that required in order to achieve the desired therapeutic effect and gradually increase the dosage until the desired effect is achieved.

The present invention is illustrated by the following examples. It is to be understood that the particular examples, materials, amounts, and procedures are to be interpreted broadly in accordance with the scope and spirit of the invention as set forth herein.

EXAMPLES

Example 1

This Example describes the synthesis of IL-37 Fc constructs.

DNA sequences encoding human IL-37 aa 46-218 (SEQ ID NO:1), human IL-37 aa 46-206 (SEQ ID NO:2), and human IL-37 aa 53-206 (SEQ ID NO:3), as shown in Table 1, were fused to a human IgG1 sequence (SEQ ID NO:4) via a peptide linker (GGGS (SEQ ID NO: 15)) to form Structure A, Structure B, and Structure C (shown in FIG. 1C), respectively.

The human CD33 signal sequence was fused to the sequences encoding human IL-37 (SEQ ID NOs:1-3), and a human Fc region and the resulting constructs (shown in FIG. 1C) were incorporated in an expression vector having a CMV promoter. As shown in Table 1, an optional hIgG1-Fc mutations in the C1q binding region to render it non-lytic are bolded and highlighted in gray. The IL-37 Fc aa46-206 construct and IL-37 Fc aa53-206 constructs were expressed in stably transfected HEK293 cells. The IL-37 Fc aa46-218 construct did not express.

For IL-37 Fc aa46-206, a DNA sequence encoding human IL-37 aa 46-218 was fused to human IgG Fc via a peptide linker at the C-terminus (FIG. 1E). N-terminal sequence analysis suggested that the expressed protein starts at the expected N-terminus, valine 46. The purified protein migrated as a 50 kD or 100 kD band under reducing or non-reducing conditions, respectively.

For IL-37 Fc aa53-206, A DNA sequence encoding the IL-37 sequence comprising amino acids 53-206, accession #Q9NZH6, was fused to human IgG Fc via a peptide linker at the C-terminus (FIG. 1F). N-terminal sequence analysis suggested that the expressed protein starts at the expected N-terminus, lysine 53. The purified protein migrated as a 52 kD or 105 kD band under reducing or non-reducing conditions, respectively.

Methods were performed as described in, for example, Lunding et al. (Allergy 2015, 70:366-373; DOI: 10.1111/a11.12566) using IL-37Fc.

Figure 3:
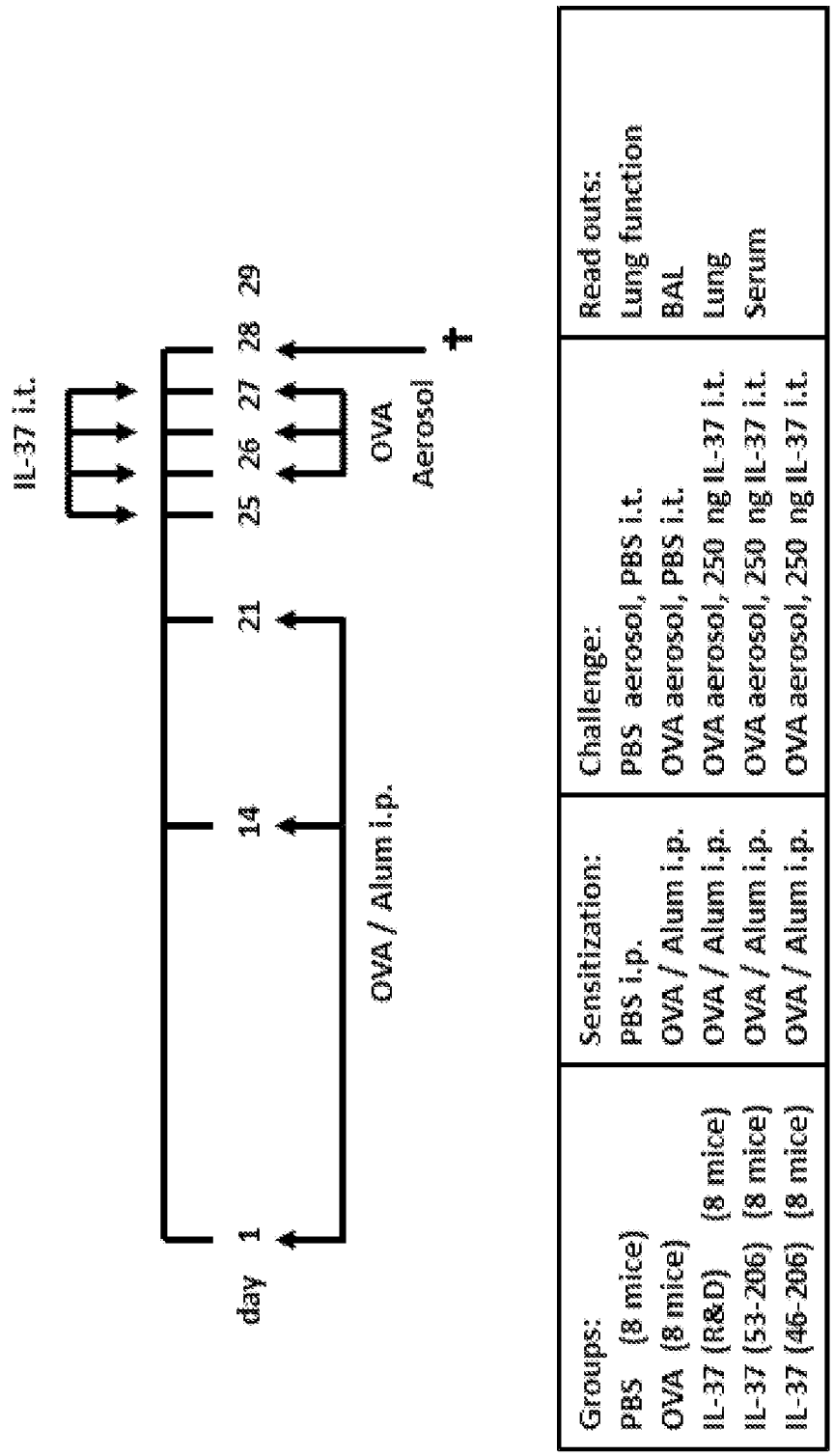
FIG. 3 shows a schematic of a treatment protocol.
Figure 4A:
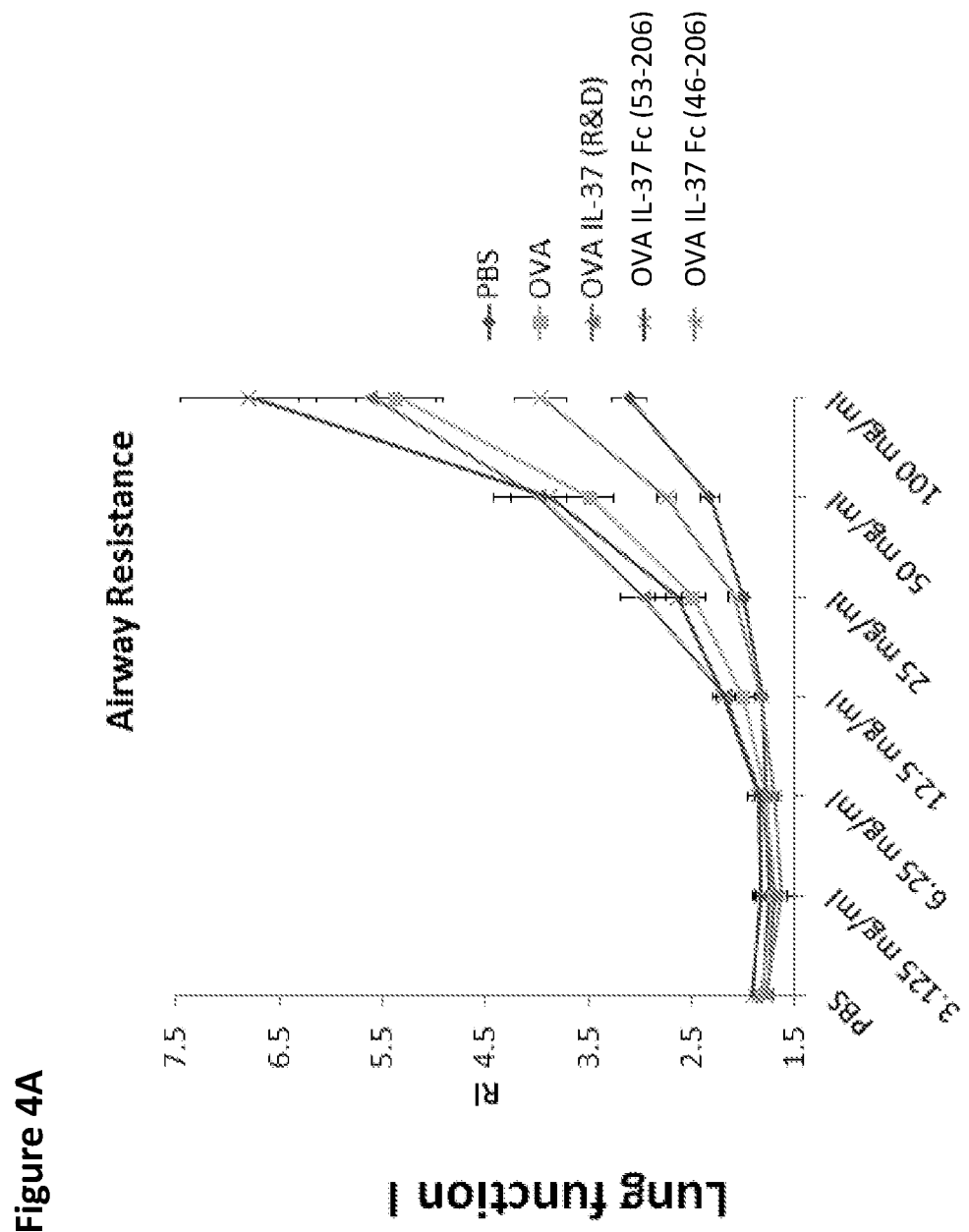
FIG. 4(A-B) shows airway resistance (FIG. 4A) and dynamic compliance (FIG. 4B), both indicators of lung function, measured in mice treated according to the treatment protocol of FIG. 3. IL-37 (R&D) includes amino acids 46-218 of IL-37 and is not fused to an Fc domain.
Figure 4B:
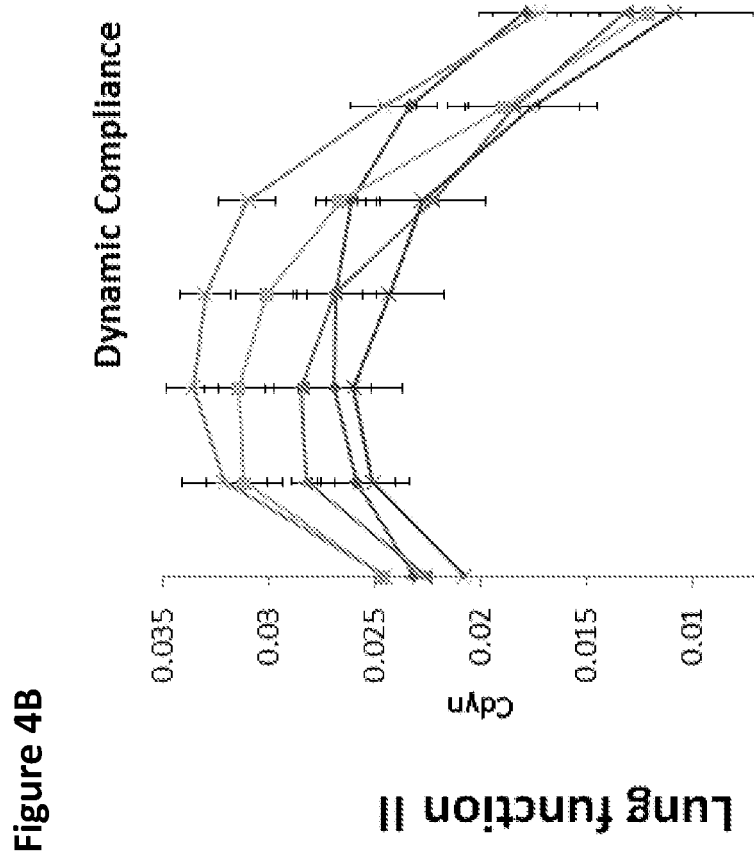
Figure 5A:
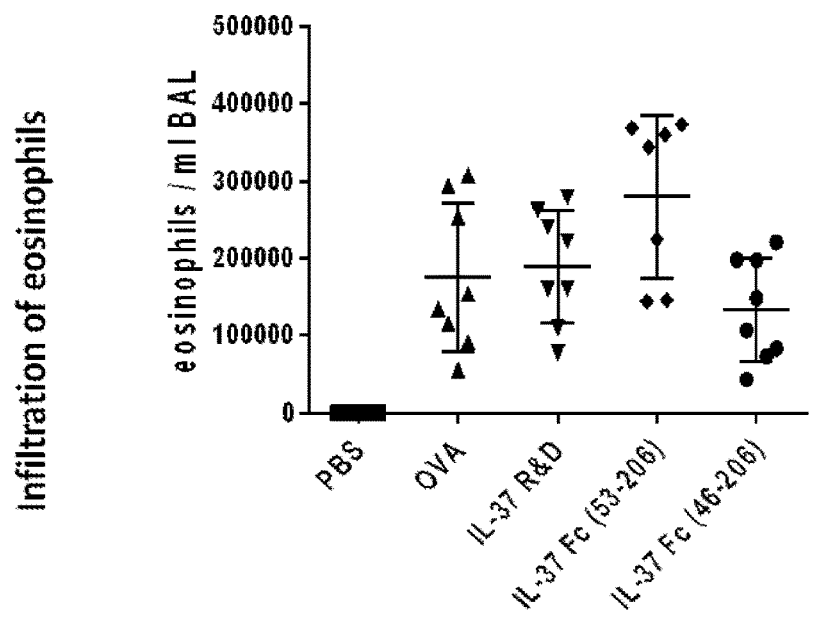
FIG. 5(A-B) shows infiltration of eosinophils in mice treated according to the treatment protocol of FIG. 3. These results show that a construct including a sequence encoding amino acids 53-206 of isoform B of human IL-37 operably linked to a sequence encoding an Fc protein ("IL-37 Fc aa53-206") provided significantly less eosinophil infiltration than a construct including a sequence encoding amino acids 46-206 of isoform B of human IL-37 operably linked to a sequence encoding an Fc protein ("IL-37 Fc aa46-206").
Figure 5B:
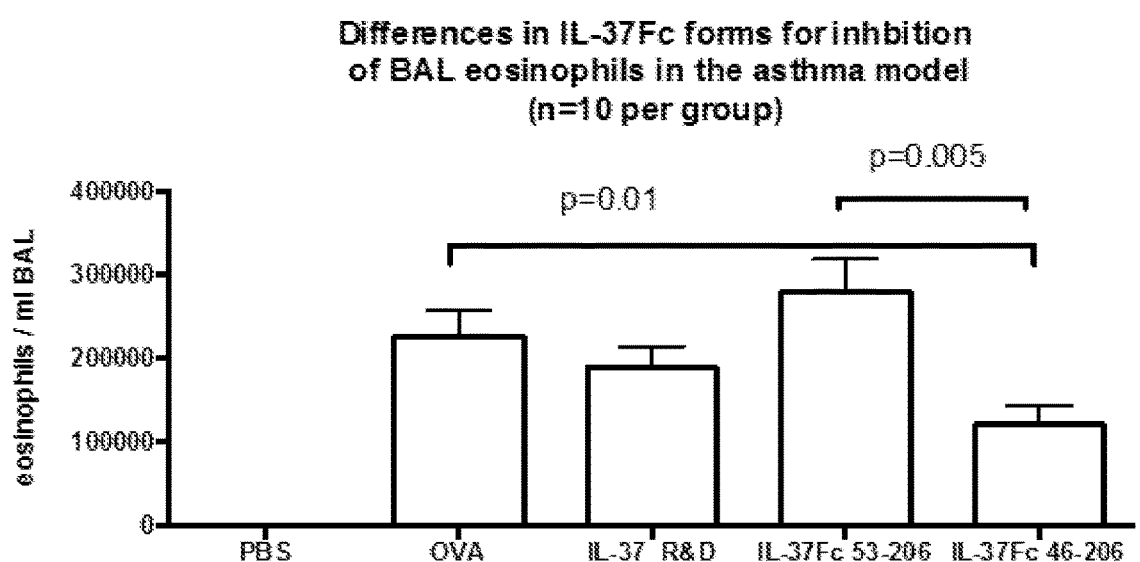

A schematic of the treatment protocol is shown in FIG. 3. Results are shown in FIGS. 4-5.

Example 4

This Example describes the effect of treating mice with an IL-37 fusion protein including amino acids 46-206 of isoform B of recombinant human IL-37 operably linked to an Fc protein ("IL-37 Fc aa46-206) and an isotype control on tumor growth, lung size, tumor weight, body weight; CD11b$^+$ cells, cDCs, NK, and CD3$^+$ T cells cells in the blood; and macrophages and CD3$^+$ T cells in the tumor.

Mice were treated with IL-37Fc or vehicle and then injected with 4T1 breast cancer tumor cells (Current Protocols in Immunology, Tumor Immunology, 20.2.15, Supple-

TABLE 1

| human IL-37 aa 46-218 | aa 46-218 of isoform B, accession #Q9NZH6 | SEQ ID NO: 1 | VHTSPKVKNLNPKKFSIHDQDHKVLVLDSGNLIA VPDKNYIRPEIFFALASSLSSASAEKGSPILLGVSKG EFCLYCDKDKGQSHPSLQLKKEKLMKLAAQKESA RRPFIFYRAQVGSWNMLESAAHPGWFICTSCNCN EPVGVTDKFENRKHIEFSFQPVCKAEMSPSEVSD |
|---|---|---|---|
| human IL-37 aa 46-206 | aa 46-206 of isoform B, accession #Q9NZH6 | SEQ ID NO: 2 | VHTSPKVKNLNPKKFSIHDQDHKVLVLDSGNLIA VPDKNYIRPEIFFALASSLSSASAEKGSPILLGVSKG EFCLYCDKDKGQSHPSLQLKKEKLMKLAAQKESA RRPFIFYRAQVGSWNMLESAAHPGWFICTSCNCN EPVGVTDKFENRKHIEFSFQPV |
| human IL-37 aa 53-206 | aa 53-206 of isoform B, accession #Q9NZH6. aa 27-200 of isoform A, accession #Q9NZH6-2. | SEQ ID NO: 3 | KNLNPKKFSIHDQDHKVLVLDSGNLIAVPDKNYIRP EIFFALASSLSSASAEKGSPILLGVSKGEFCLYCDKDK GQSHPSLQLKKEKLMKLAAQKESARRPFIFYRAQVG SWNMLESAAHPGWFICTSCNCNEPVGVTDKFENRK HIEFSFQPV |
| heavy chain portion of the antibody human IgG1-Fc sequence) | | SEQ ID NO: 4 | PKSCDKTHTCPPCPAPEAEGAPSVFLFPPK PKDTLMISRTPEVTCVVVDVSHEDPEVKFN WYVDGVEVHNAKTKPREEQYNSTYRVVSV LTVLHQDWLNGKEYKCKVSNKALPAPIEKTI SKAKGQPREPQVYTLPPSRDELTKNQVSLTC LVKGFYPSDIAVEWESNGQPENNYKATPP VLDSDGSFFLYSKLTVDKSRWQQGNVFSCS VMHEALHNHYTQKSLSLSPGK |
| non-lytic hIgG1-Fc sequence | | SEQ ID NO: 5 | PKSCDKTHTCPPCPAPEAEGAPSVFLFPPK PKDTLMISRTPEVTCVVVDVSHEDPEVKFN WYVDGVEVHNAKTKPREEQYNSTYRVVSV LTVLHQDWLNGKAYACAVSNKALPAPIEKTI SKAKGQPREPQVYTLPPSRDELTKNQVSLTC LVKGFYPSDIAVEWESNGQPENNYKATPP VLDSDGSFFLYSKLTVDKSRWQQGNVFSCS VMHEALHNHYTQKSLSLSPGK |
| CD33 signal sequence | | SEQ ID NO: 6 | MPLLLLLPLLWAGALA |

Example 2

Figure 2:
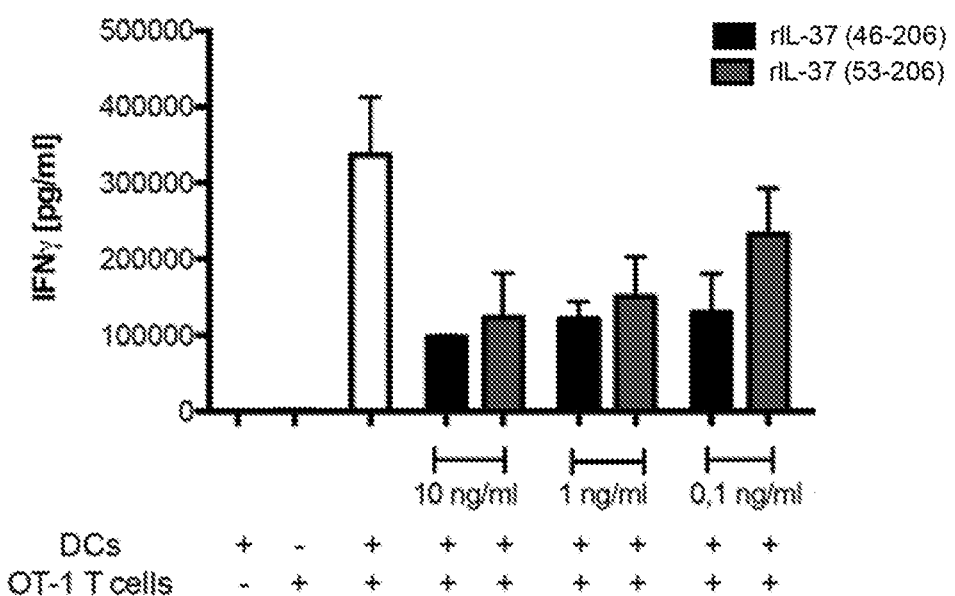
FIG. 2 shows that a construct including amino acids 53-206 of isoform B of human IL-37 ("IL-37 aa53-206" or "rIL-37 (53-206)") and a construct including amino acids 46-206 of isoform B of human IL-37 ("IL-37 aa46-206" or "rIL-37 (46-206)") exhibit near similar activities. Neither construct includes an Fc domain.

This Example describes the comparison of efficacy of IL-37 proteins.
Results are shown in FIG. 2.

Example 3

This Example describes the effect of treating mice with IL-37 fusion proteins including different isoforms of IL-37 on lung function and bronchoalveolar lavage (BAL) fluid eosinophil percentages. These data can provide information regarding the effects of IL-37 fusion proteins on experimental asthma.

ment 39), which spontaneously metastasize in different organs. Mice were treated every 3 days with IL-37Fc (1 or 5 μg per mouse). After approximately 28-30 days, liver, lung, spleen, lymph node were removed, cut into small pieces and treated with a 30 minute Collagenase-DNAse digestion at 37° C. After digestion, the organs were passed through a 100 μm and a 30 μm cell strainer to obtain single-cell suspensions. After centrifugation, red blood cells were lysed for 2 minutes and the suspension centrifuged one more time.

After the preparation of single cells, 6-Thioguanine, a cytostatic drug that kills normal cells, was added to the single-cell suspension in different ratios with medium. For example, when analyzing the lung, the whole-lung single cell suspension was diluted 1:10, 1:100, and 1:1000 in medium containing the 6-Thioguanine and plated into 6-well plates (3 wells per organ). Cells which lack resistance against the cytostatic drug die, and only the tumor cells proliferate and form macroscopic colonies.

After 7-10 days, the colonies are visible by eye. The wells were stained the crystal violet. After 10 minutes fixation in 70% ethanol, the formed colonies are clearly stained and were counted and the resulting number was normalized.

Figure 6:
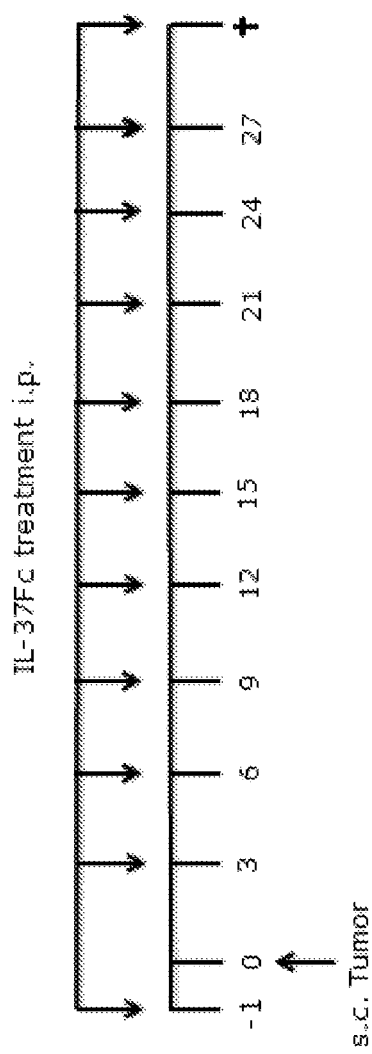
FIG. 6 shows a schematic of a treatment protocol. 1 microgram (m) of IL-37 Fc aa46-206 or Isotype-Control was injected intraperitoneally (i.p.) into mice every 3 days.
Figure 7:
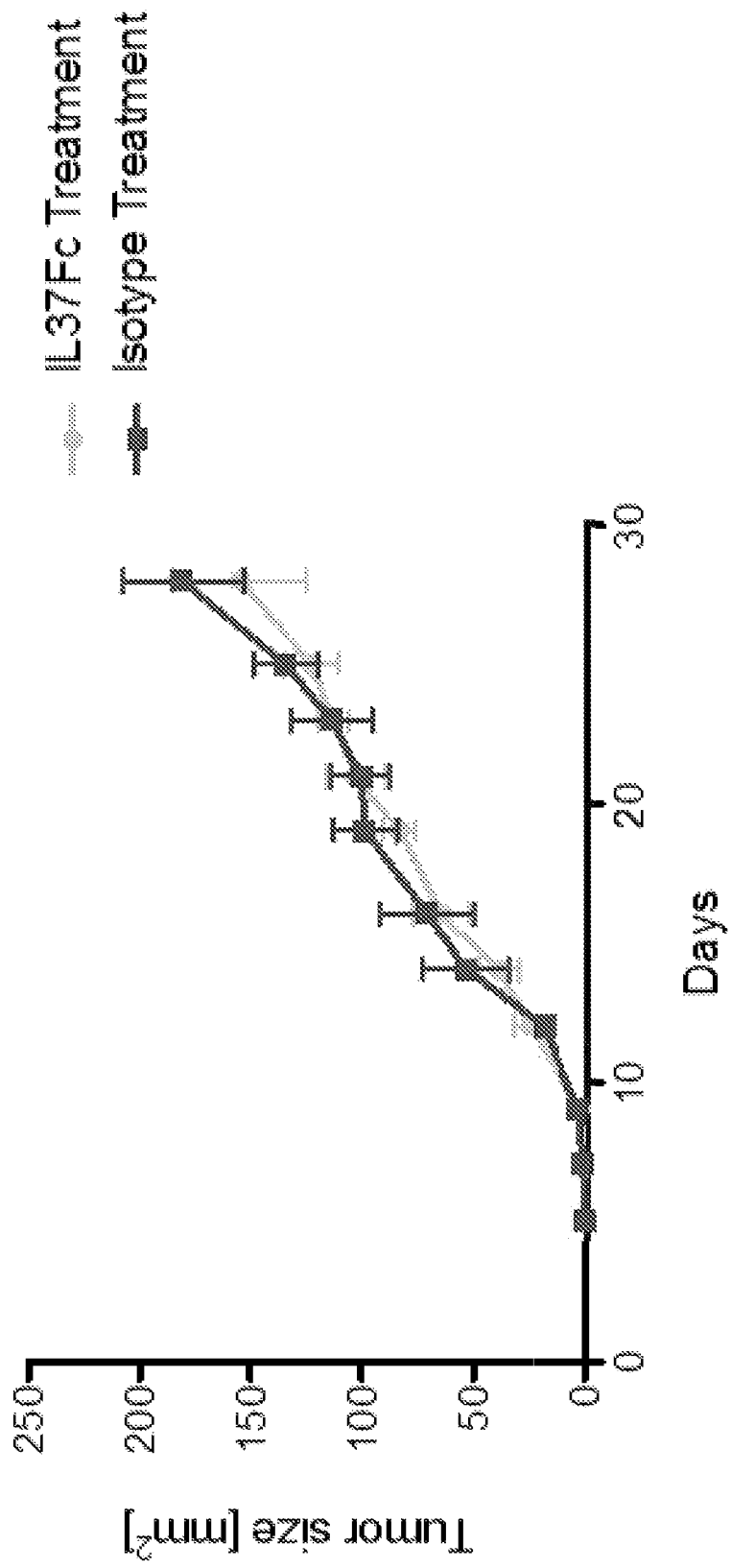
FIG. 7 shows IL-37 Fc aa46-206 treatment, according to the protocol of FIG. 6, did not alter the tumor growth of 4T1 tumor cells.
Figure 8:
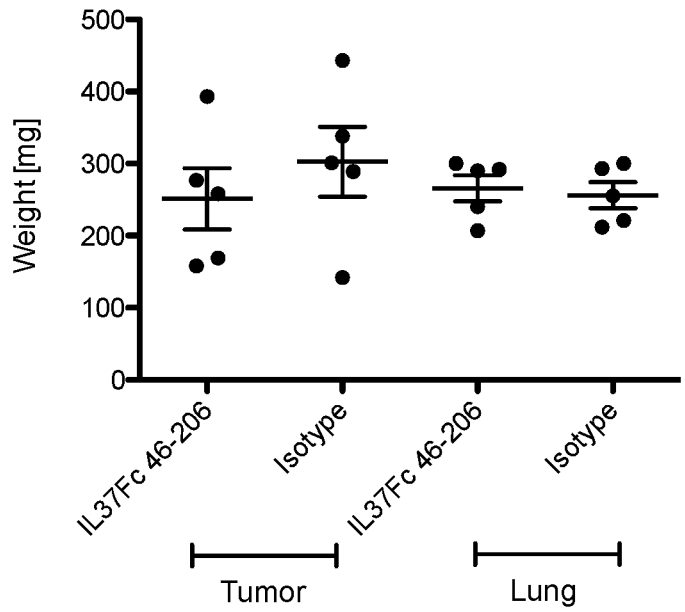
FIG. 8 shows IL-37 Fc aa46-206 treatment, according to the protocol of FIG. 6, did not change the weight of the lungs, and no significant decrease in tumor weight was observed.
Figure 9:
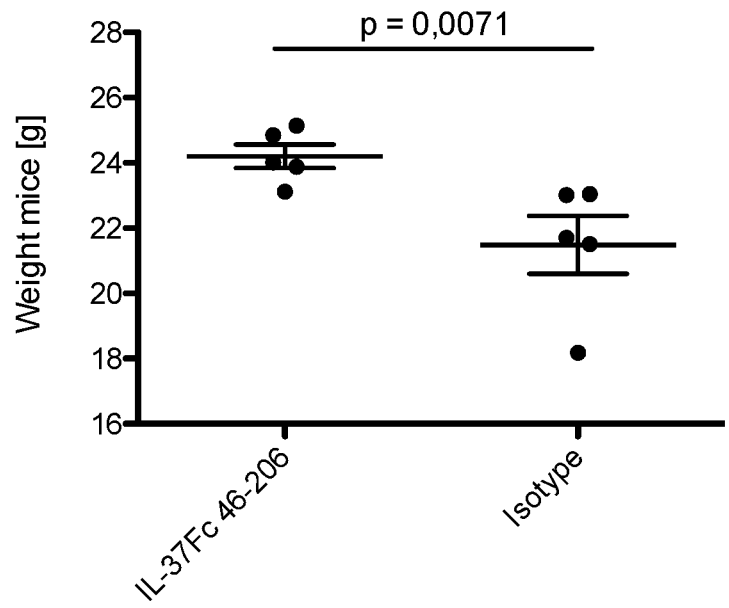
FIG. 9 shows IL-37 Fc aa46-206 treated mice, treated according to the protocol of FIG. 6, did not lose as much weight as to isotype-treated mice.
Figure 10:
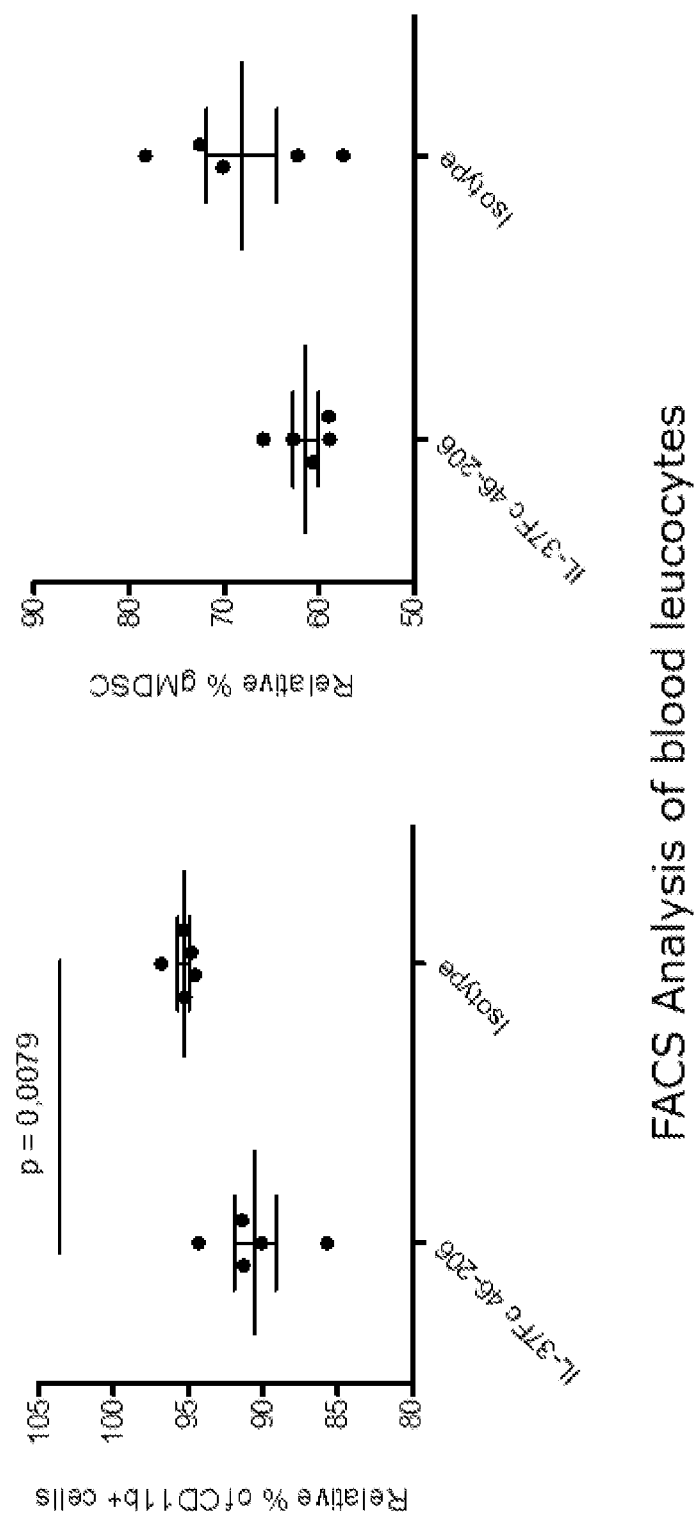
FIG. 10 shows IL-37 Fc aa46-206 treated mice, treated according to the protocol of FIG. 6, demonstrated a significantly lower percentage of CD11b$^+$ cells in the blood.
Figure 11:
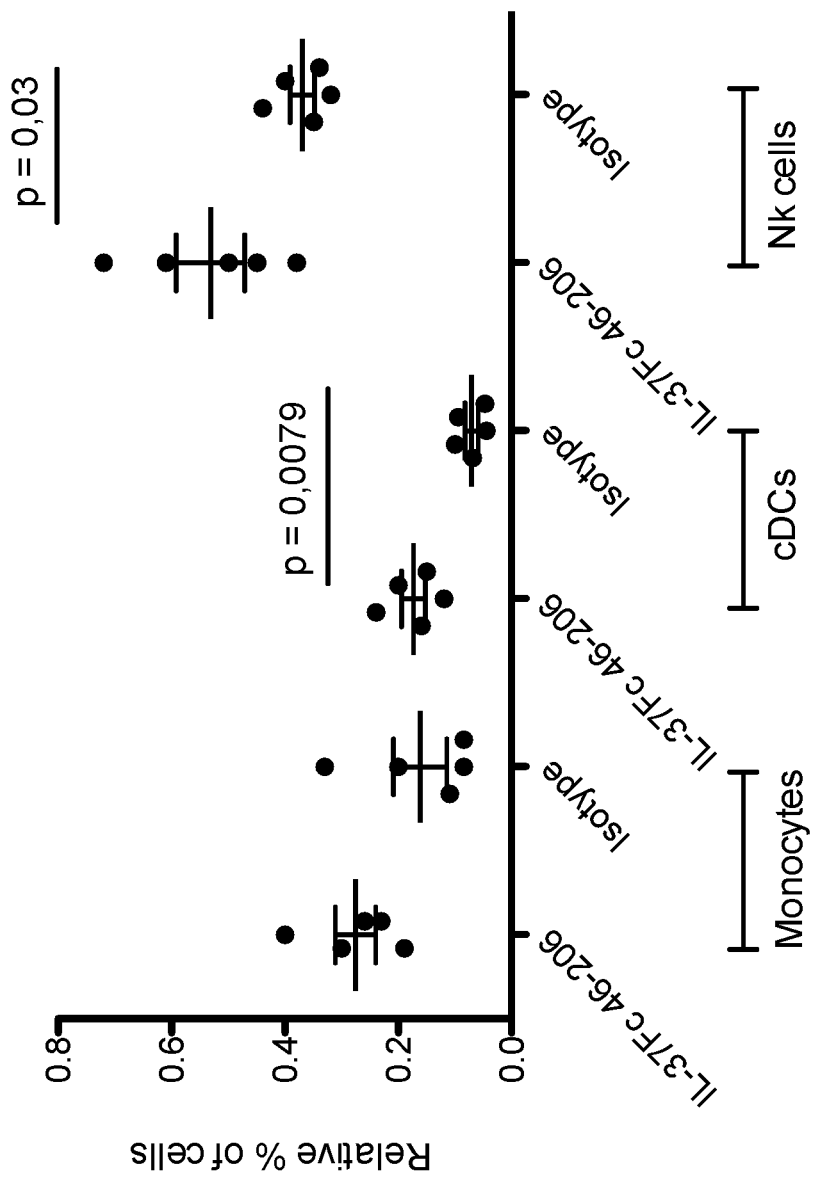
FIG. 11 shows IL-37 Fc aa46-206 treated mice, treated according to the protocol of FIG. 6, demonstrated significantly increased percentages of cDCs and NK cells in the blood, as measured by flow cytometry.
Figure 12:
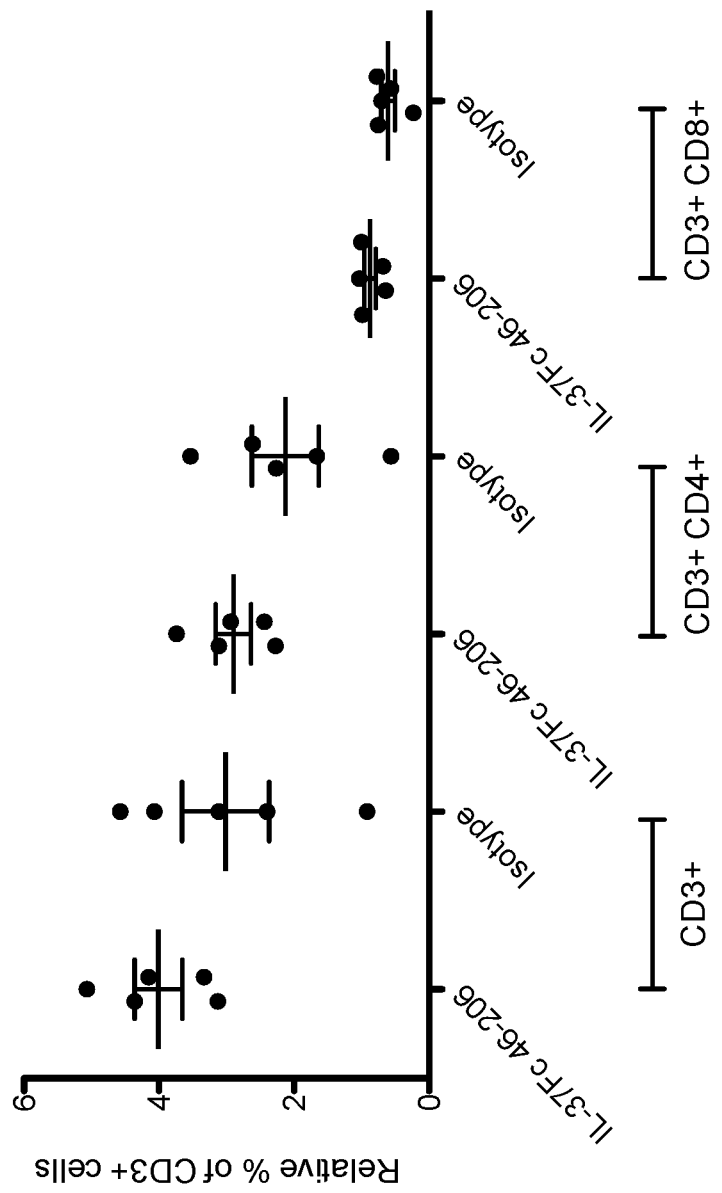
FIG. 12 shows a change in the percentage of CD3$^+$ T cells in the blood of IL-37 Fc aa46-206 treated mice, treated according to the protocol of FIG. 6, when compared to isotype-treated mice, as measured by flow cytometry.
Figure 13:
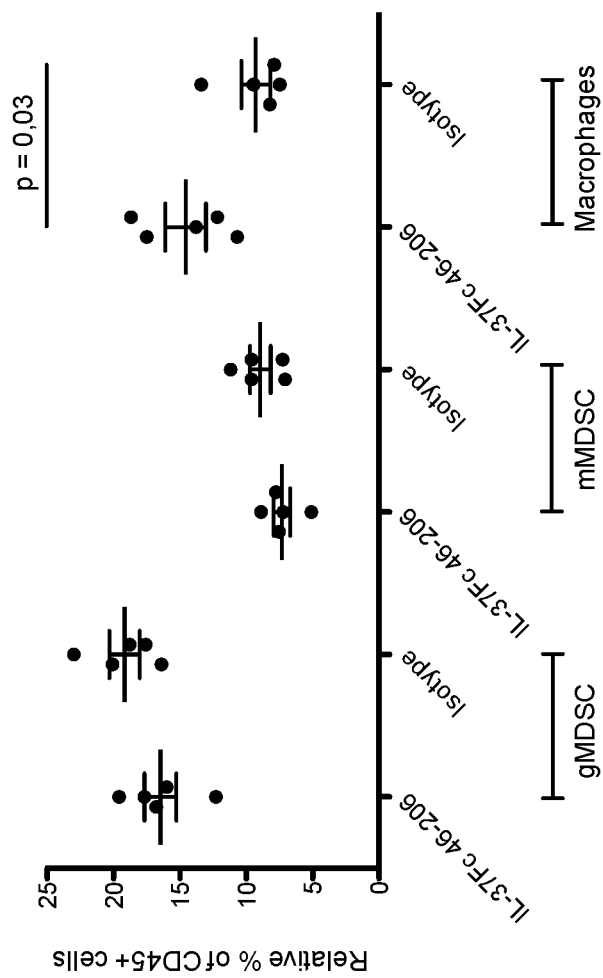
FIG. 13 shows a significant increase in macrophages in a tumor in IL-37 Fc aa46-206 treated mice, treated according to the protocol of FIG. 6, when compared to isotype-treated mice, as measured by flow cytometry.
Figure 14:
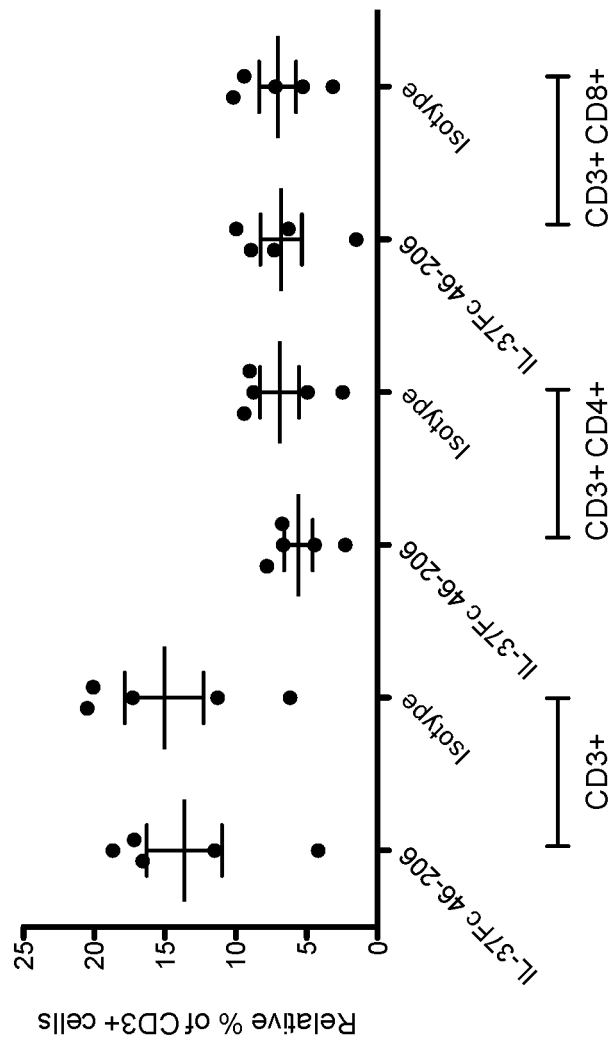
FIG. 14 shows no differences in the percentages of CD3$^+$ T cells in the tumor were observed tumor in IL-37 Fc aa46-206 treated mice, treated according to the protocol of FIG. 6, when compared to isotype-treated mice.

A schematic of the treatment protocol is shown in FIG. 6. Results are show in FIGS. 7-14.

Example 5

Figure 15:
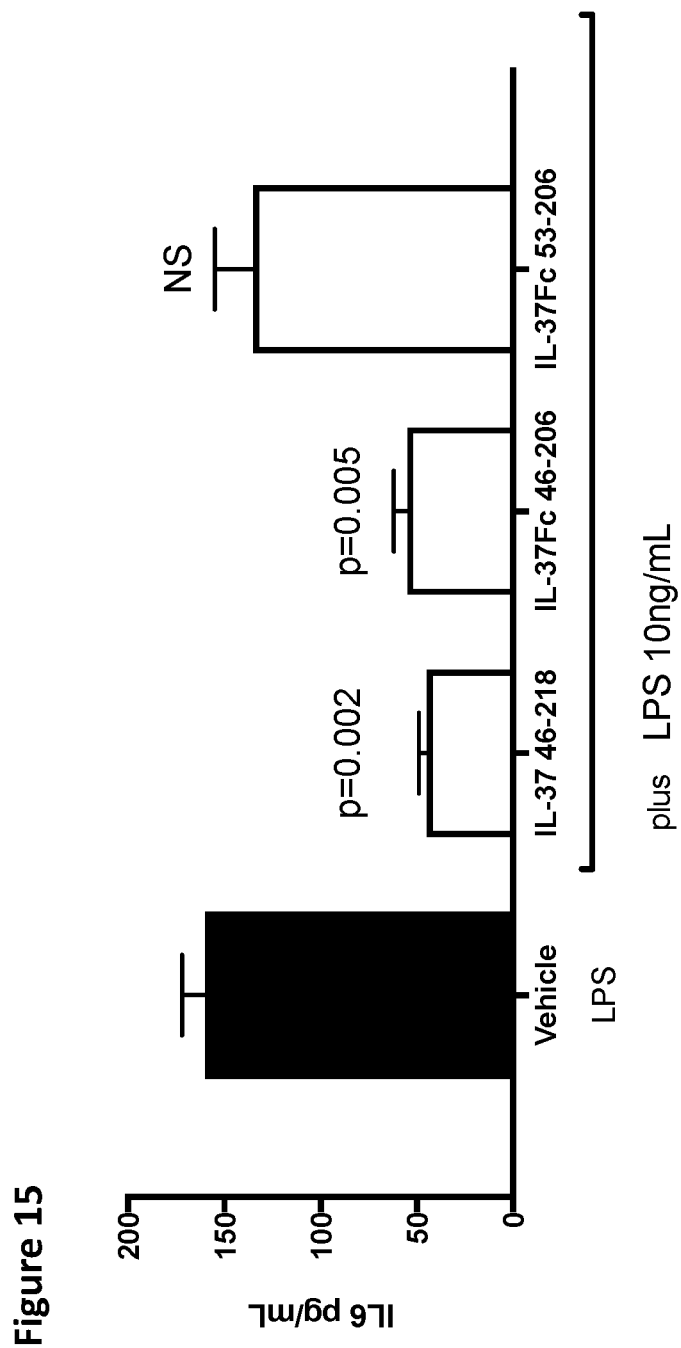
FIG. 15 shows differences in the effects of different IL-37Fc constructs on LPS-induced IL-6 in human blood monocyte-derived M1 differentiated macrophages (donor 34). Cells in each group were treated with 10 ng/mL LPS.

This Example describes the effect of different IL-37Fc constructs on LPS-induced (10 ng/mL) IL-6 in human blood-monocyte derived M1 differentiated macrophages. The methods were performed as described in Li et al. 2015, PNAS USA 112(8):2497-2502. Results are shown in FIG. 15.

Example 6

Figure 16:
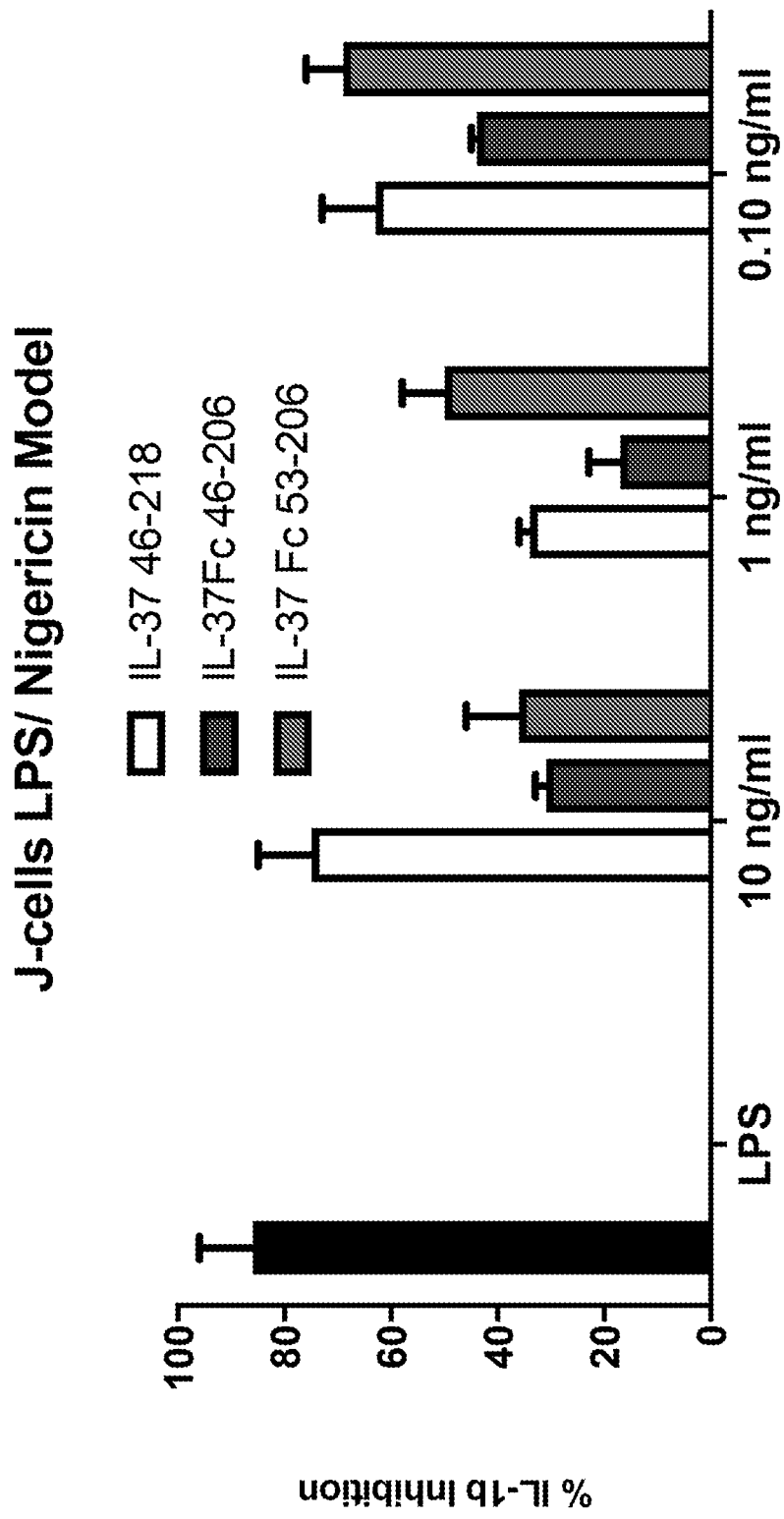
FIG. 16 shows differences in the effects of different IL-37Fc constructs on IL-1β in J774A.1 cells stimulated with LPS/nigericin.

This Example describes the effect of different IL-37Fc constructs on IL-1β in J774A.1 cells stimulated with LPS/ nigericin. The methods were performed as described in Marchetti et al. 2018, PNAS USA 115(7):E1530-E1539. Results are shown in FIG. 16.

Example 7

Figure 17:
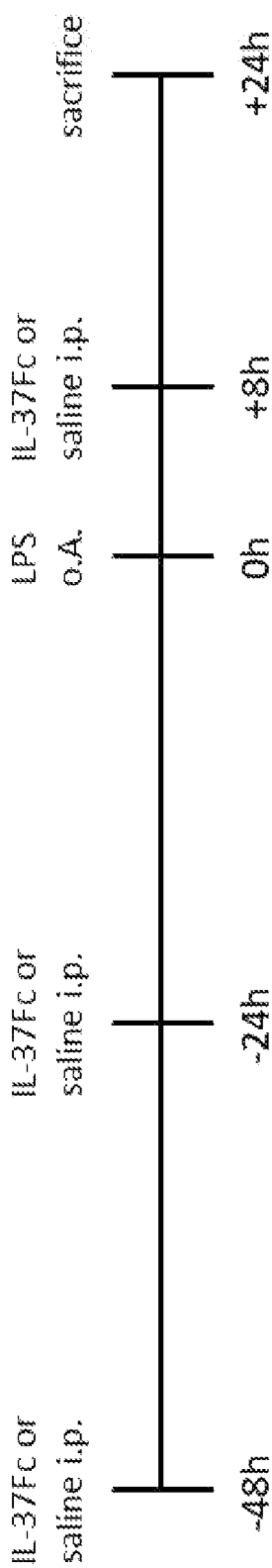
FIG. 17 shows a treatment protocol in which IL-37Fc is administered intraperitoneally to mice as a model of systemic treatment for lung disease, and LPS was used to simulate acute lung injury.
Figure 18A:
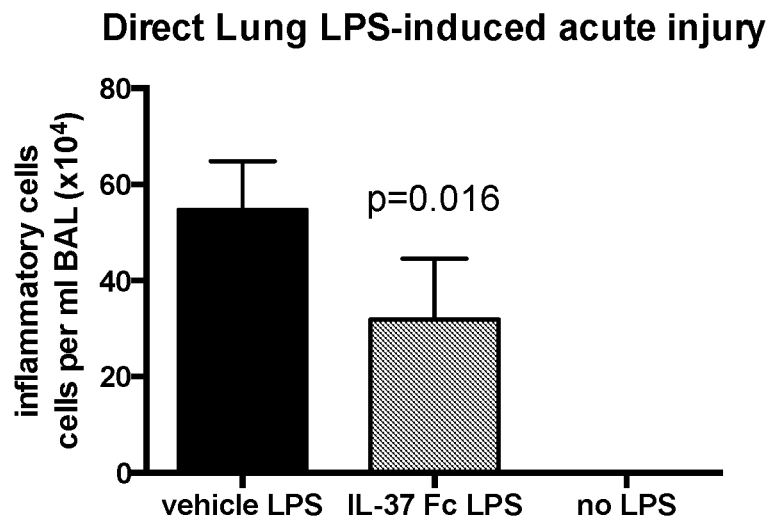
FIG. 18(A-B) shows the results of administering IL-37Fc (human IL-37 Fc aa46-206) intraperitoneally, as shown in FIG. 17, on the number of inflammatory cells per milliliter of bronchoalveolar lavage (BAL) after challenge with LPS.
Figure 18B:
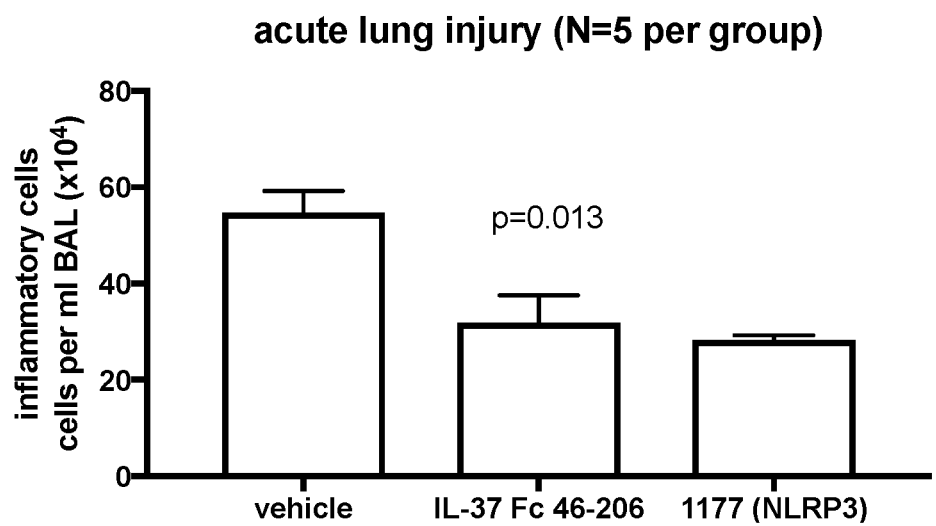
Figure 19:
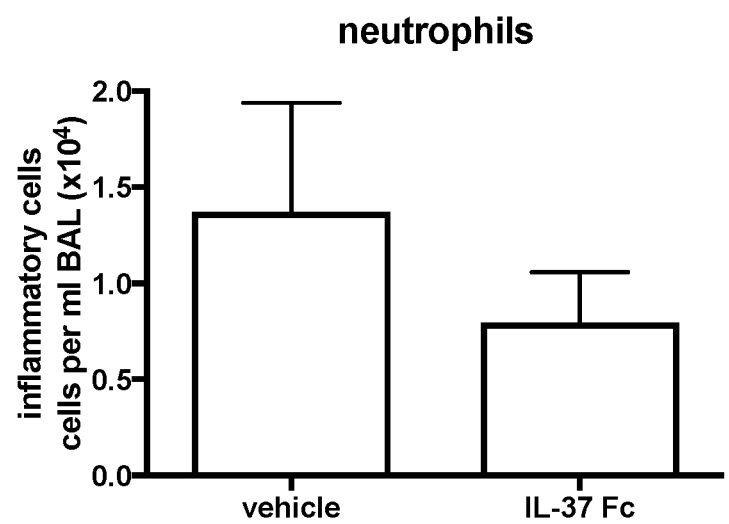
FIG. 19 shows the results of administering IL-37Fc (human IL-37 Fc aa46-206) intraperitoneally, as shown in FIG. 17, on the number of inflammatory cells per milliliter of bronchoalveolar lavage (BAL) after challenge with LPS.
Figure 20:
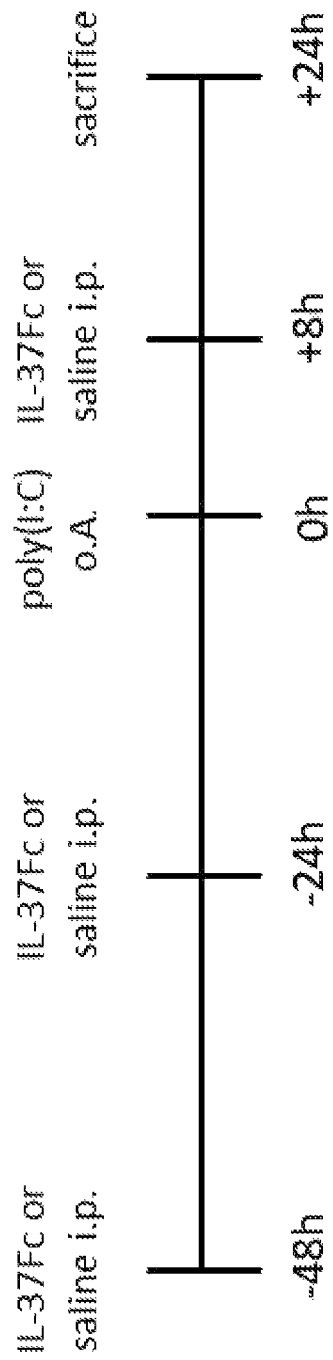
FIG. 20 shows a treatment protocol in which IL-37Fc (human IL-37 Fc aa46-206) is administered intraperitoneally to mice as a model of systemic treatment for lung disease, and Poly I:C was used to simulate of acute lung injury.
Figure 21A:
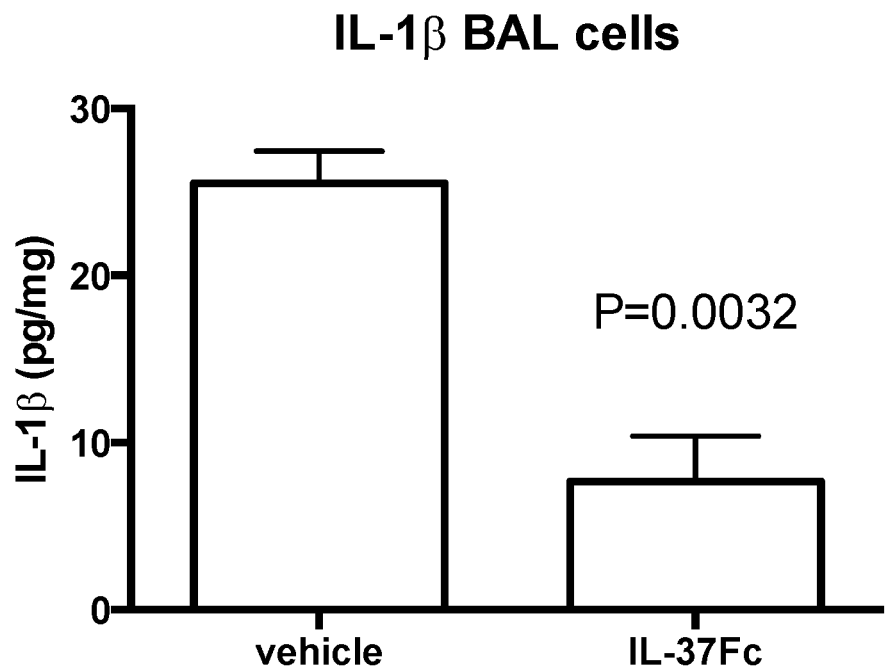
FIG. 21(A-H) shows exemplary results of administering IL-37Fc (human IL-37 Fc aa46-206) intraperitoneally, as shown in FIG. 20, on IL-1β in bronchoalveolar lavage (BAL) cells (FIG. 21A, FIG. 21B), KC (the mouse homologue of the human neutrophil chemokine IL-8) levels in BAL cells (FIG. 21C), IL-1β levels in whole lung homogenates (FIG. 21D), IL-1α levels in whole lung homogenates (FIG. 21E), IL-6 levels in whole lung homogenates (FIG. 21F), KC levels in whole lung homogenates (FIG. 21G), and TNFα levels in whole lung homogenates (FIG. 21H) after challenge with Poly I:C.
Figure 21B:
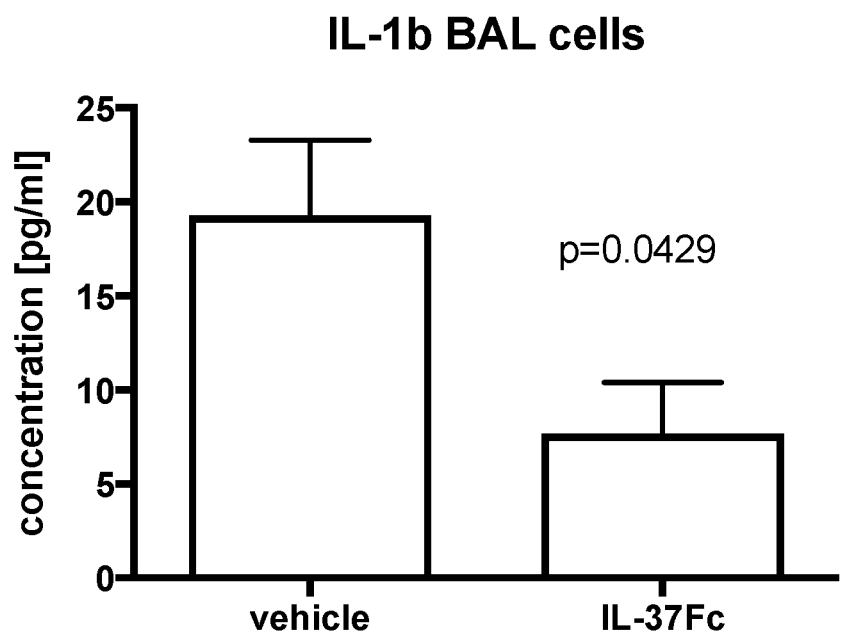
Figure 21C:
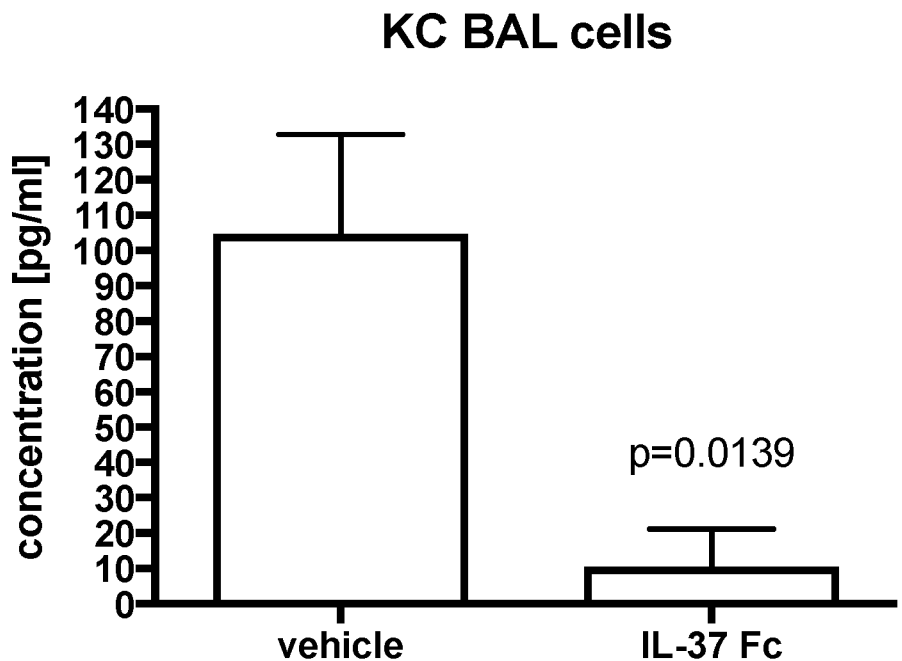
Figure 21D:
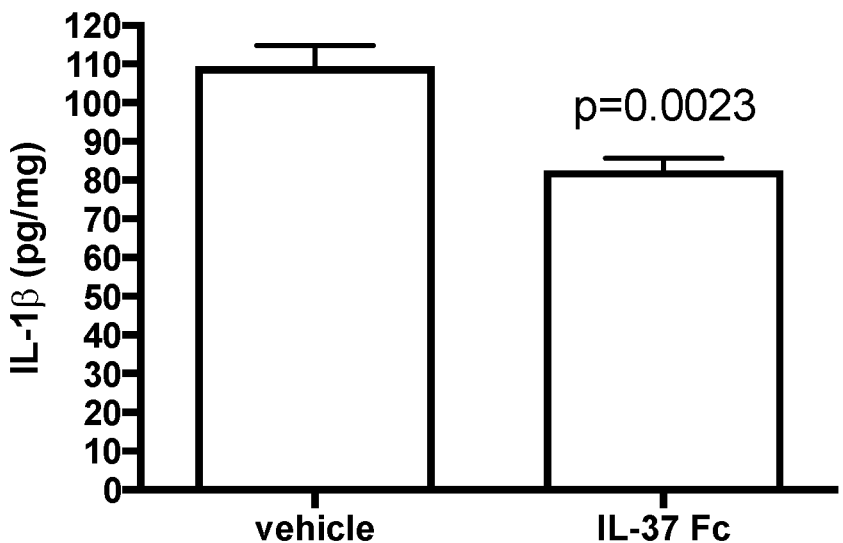
Figure 21E:
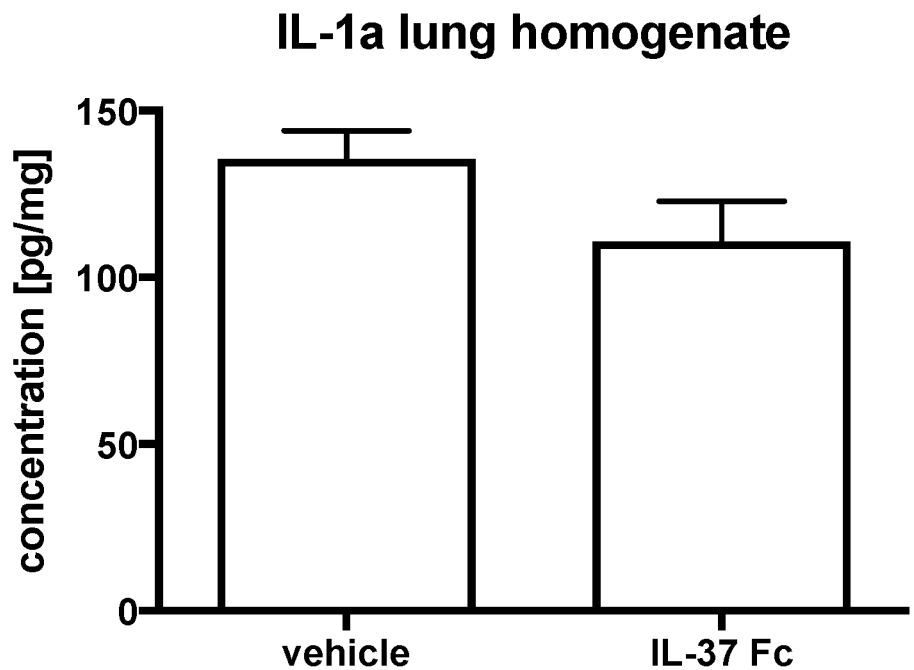
Figure 21F:
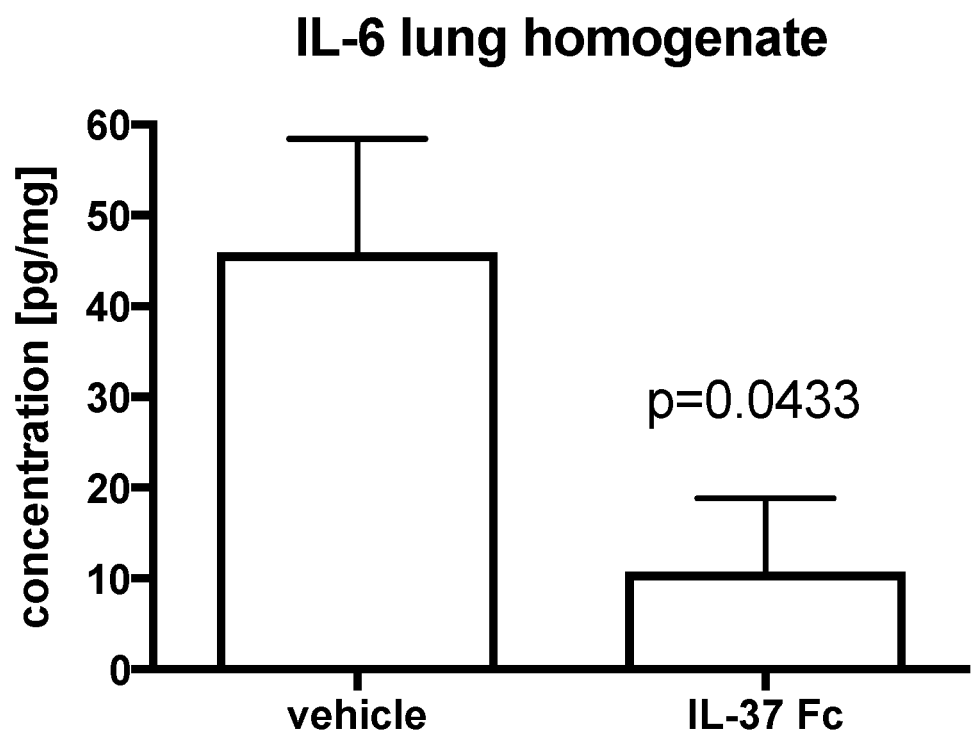
Figure 21G:
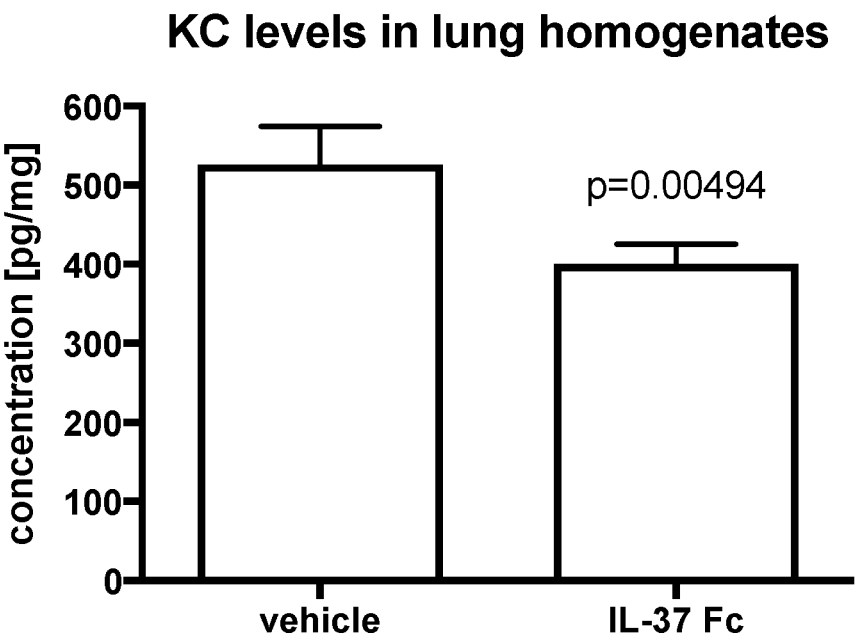
Figure 21H:
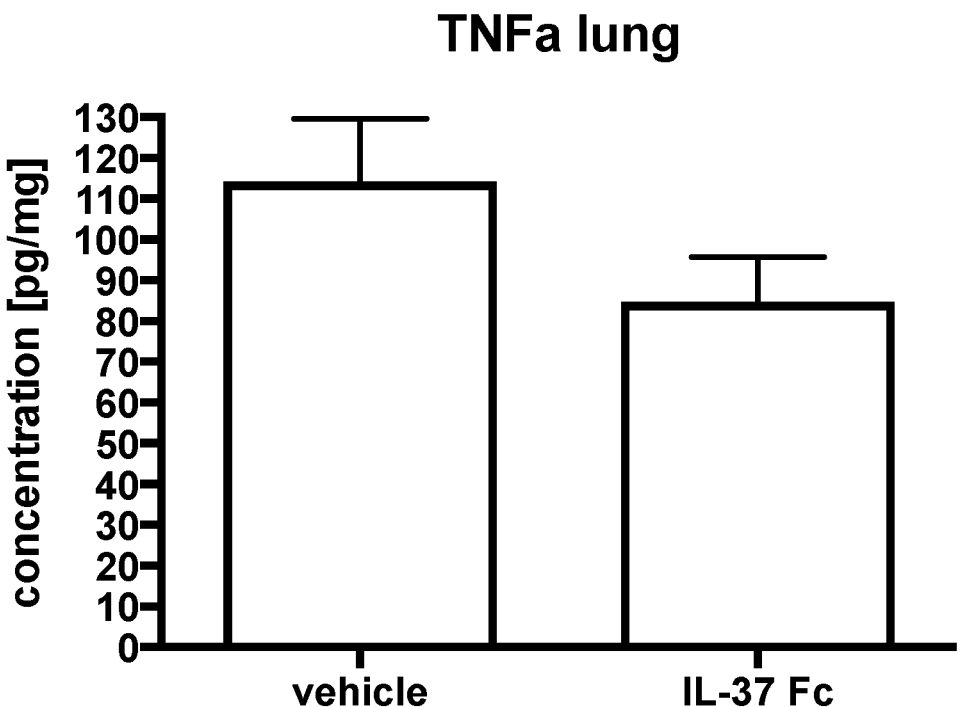

This Example describes the effect of IL-37Fc (human IL-37 Fc aa46-206) in models of lung disease including, for example, asthma. In contrast to Example 3 where the IL-37Fc was directly administered into the lung, in this Example, IL-37Fc was administered intraperitoneally as a model of systemic treatment for lung disease. Acute lung injury was simulated using two models: LPS (FIG. 17) and Poly I:C (FIG. 20). These models of acute lung injury are commonly used as a model for sepsis-related diseases, but they are also relevant for any lung disease in which neutrophils invade the lung and cause damage. Results are shown in FIG. 18 and FIG. 19 (for LPS) and FIG. 21 (for Poly I:C).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A fusion protein comprising:
   a fragment of IL-37, wherein the fragment of IL-37 consists of amino acids 46-206 of isoform B of IL-37 and wherein the fragment of IL-37 consists of SEQ ID NO:2; and
   a heavy chain portion of an antibody.

2. The fusion protein of claim 1, wherein the heavy chain portion of an antibody comprises an IgG Fc region.

3. The fusion protein of claim 1, wherein the heavy chain portion of an antibody comprises an IgG1 Fc region.

4. The fusion protein of claim 3, wherein the IgG1 Fc region comprises SEQ ID NO:4.

5. The fusion protein of claim 2, wherein the IgG Fc region comprises mutations to at least one of a complement C1q binding site and an Fc gamma receptor (FcγR) binding site.

6. The fusion protein of claim 3, wherein the IgG1 Fc region comprises L234A and L235A (LALA) substitutions.

7. The fusion protein of claim 3, wherein the IgG1 Fc region comprises SEQ ID NO:5.

8. The fusion protein of claim 1, the fusion protein comprising a peptide linker.

9. The fusion protein of claim 8, wherein the peptide linker comprises the amino acid sequence GGGS (SEQ ID NO: 15).

10. The fusion protein of claim 8, wherein the peptide linker connects the fragment of IL-37 and the heavy chain portion of an antibody.

11. The fusion protein of claim 1, the fusion protein comprising a signal peptide.

12. The fusion protein of claim 11, wherein the signal peptide comprises a CD33 signal peptide.

13. The fusion protein of claim 12, wherein the CD33 signal peptide comprises SEQ ID NO:6.

* * * * *